US005759814A

United States Patent [19]
Burke et al.

[11] Patent Number: 5,759,814
[45] Date of Patent: Jun. 2, 1998

[54] EXPRESSION OF RECOMBINANT GLYCOPROTEIN B FROM HERPES SIMPLEX VIRUS

[75] Inventors: Rae L. Burke, San Francisco; Carol Pachl, Oakland; Pablo D.T. Valenzuela, San Francisco, all of Calif.

[73] Assignee: Chiron Corporation, Emeryville, Calif.

[21] Appl. No.: 465,467

[22] Filed: Jun. 5, 1995

Related U.S. Application Data

[62] Division of Ser. No. 351,875, Dec. 8, 1994, Pat. No. 5,648,079, which is a continuation of Ser. No. 138,717, Oct. 18, 1993, abandoned, which is a continuation of Ser. No. 993,415, Dec. 21, 1992, abandoned, which is a division of Ser. No. 587,179, Sep. 20, 1990, Pat. No. 5,244,792, which is a continuation of Ser. No. 921,730, Oct. 20, 1986, abandoned, which is a continuation-in-part of Ser. No. 597,784, Apr. 6, 1984, abandoned.

[51] Int. Cl.⁶ .................................................. C12P 21/02
[52] U.S. Cl. .............................. 435/69.3; 435/69.1; 435/5
[58] Field of Search ........................... 424/199.1, 231.1, 424/279.1, 283.1, 186.1, 184.1; 435/69.1, 69.3, 235.1, 252.3; 514/2, 8; 530/350, 395

[56] References Cited

U.S. PATENT DOCUMENTS

| | | |
|---|---|---|
| 4,172,125 | 10/1979 | Audibert et al. |
| 4,317,811 | 3/1982 | Bertland et al. |
| 4,374,127 | 2/1983 | Larson et al. |
| 4,452,734 | 6/1984 | Larson et al. ............................ 530/395 |
| 4,606,918 | 8/1986 | Allison et al. ........................ 424/279.1 |
| 4,642,333 | 2/1987 | Person. |
| 4,661,349 | 4/1987 | Kino et al. |
| 4,724,146 | 2/1988 | Kino et al. |
| 4,891,315 | 1/1990 | Watson et al. ......................... 435/69.3 |
| 5,171,568 | 12/1992 | Burke et al. |
| 5,244,792 | 9/1993 | Burke et al. ........................... 435/69.3 |

FOREIGN PATENT DOCUMENTS

| | | |
|---|---|---|
| 133063 | 2/1985 | European Pat. Off. |
| 168662 | 1/1986 | European Pat. Off. |

OTHER PUBLICATIONS

Burke et al. The Influence of Adjuvants on the Therapeutic Efficacy of a Recombinat Genital Herpes Vaccine J. Inf. Dis. 170:1110–1119 (1994).
Sanchez Pescador et al. The Effect of Adjuvants on the Efficacy of a Recombinat Herpes Simplex Virus Glycoprotei Vaccine. J. of Immunology 141:1720–1727 1988.
Byars, et al. Vaccinating Guinea Pigs with Recombinant Glycoprotein D of Herpes Simplex Virus in a Efficacious Adjuvant Formulation Elicits Protection Against Vaginal Infection, Vaccine 12:200–209, 1994.
Berman et al., *Science* (1985) 227:1490–1492.
Bzik et al., *Virology* (1984) 133:301–314.
Cappel et al., *J. Med. Virol.* (1985) 16: 137–145.
Chan, *Immunology* (1983) 49:343–352.
Cohen et al., *J. Virol.* (1984) 49:102–108.
DeLucca et al., Virology (1982) 122:411–423.
Dundarov et al., *Devel. Biol. Standard.* (1982) 52:351–357.
Eberle et al., *J. Infect. Dis.* (1983) 148:436–444.
Hilfenhaus et al., *Devel. Biol. Standard.* (1982) 52:321–331.
Lasky et al., *Biotechnology* (Jun. 1984) pp. 527–532.
Marsden et al., *J. Virol.* (1978) 28:624–642.
Pellet et al., *J. Virol.* (1985) 53:243–253.
Roizman et al., *Ann. Rev. Genet.* (1979) 13:25–57.
Ruyechan et al., *J. Virol.* (1979) 29:677–697.
Skare et al., *Virology* (1977) 76:581–595.
Skinner et al., *Devel. Biol. Standard.* (1982) 52:333–344.
Watson et al., *Science* (1982) 218:381–384.
Weis et al., *Nature* (1983) 302:72–74.

*Primary Examiner*—Mary E. Mosher
*Attorney, Agent, or Firm*—Roberta L. Robins; Barbara G. McClung; Robert P. Blackburn

[57] ABSTRACT

The glycoprotein B ("gB") and analogs thereof are provided by recombinant DNA technology. Oligonucleotide sequences are provided coding the glycoprotein, its precursor and fragments thereof. Methods and compositions are disclosed for the production of the glycoprotein and analogous proteins as well as oligonucleotide sequences, which may be used for probes or other applications, and particularly may be used for vaccines.

10 Claims, 16 Drawing Sheets

```
-308 TCGCGAGCTCATTATCGCCACCACACTCTTTGCGTCGGTCTACCGGTGCGGGGAGCTTGA
     TCGCGAGCTGATTATCGCCACCACACTCTTTGCCTCGGTCTACCGGTGCGGGGAGCTCGA

GTTGCGCCGCCCCGACTGCAGCCGCCCGACCTCCGAAGGTCTGTACCGCTACCCGCCGG
     GTTGCGCCGCCCGGACTGCAGCCGCCCGACCTCCGAAGGTCGTTACCGTTACCCGCCCG

-189 GCGTGTACCTCACGTACAACTCCGACTGTCCGCTGGTGGCCATCGTCGAGAGCGGCCCCG
     GCGTATATCTCACGTACGACTCCGACTGTCCGCTGGTGGCCATCGTCGAGAGCGCCCCCG

ACGGCTGCATCGGACCCCGCTCGGTCGTGGTTTACGACCGAGACGTTTTTTCCATCCTC
     ACGGCTGTATCGGCCCCCGGTCGGTCGTGGTCTACGACCGAGACGTTTTCTCGATCCTC

-70  TACTCGGTCCTGCAGCACCTCGCCCCCAGACTAGCGGGCGGCGGGAGCGACGCGCCCCCG
     TACTCGGTCCTCCAGCACCTCGCCCCCAGGCTACCTGACGGGGGGCACGACGGGCCCCG
```

Fig. 4A (sequence alignment with amino acid translations — codons and protein sequences as shown)

FIG. 4A

```
       Phe Glu Gln Pro Arg Arg Cys Pro Thr Arg Pro Glu Gly Gln Asn
   364 TTT GAG CAG CCG CGC CGC TGC CCG ACG CGC CCG GAG GGG CAG AAC
       TTC GAG CAG CCG CGC CGC TGC CCG ACC CGG CCC GAG GGT CAG AAC
       Phe Glu Gln Pro Arg Arg Cys Pro Thr Arg Pro Glu Gly Gln Asn

Tyr Thr Glu Gly Ile Ala Val Val Phe Lys Glu Asn Ile Ala Pro   151
       TAC ACG GAG GGC ATC GCG GTG GTC TTC AAG GAG AAC ATC GCC CCG
       TAC ACG GAG GGC ATC GCG GTG GTC TTC AAG GAG AAC ATC GCC CCG
       Tyr Thr Glu Gly Ile Ala Val Val Phe Lys Glu Asn Ile Ala Pro

Tyr Lys Phe Lys Ala Thr Met Tyr Tyr Lys Asp Val Thr Val Ser
   454 TAC AAA TTC AAG GCC ACC ATG TAC TAC AAA GAC GTG ACC GTG TCG
       TAC AAG TTC AAG GCC ACC ATG TAC TAC AAA GAC GTC ACC GTT TCG
       Tyr Lys Phe Lys Ala Thr Met Tyr Tyr Lys Asp Val Thr Val Ser

Gln Val Trp Phe Gly His Arg Tyr Ser Gln Phe Met Gly Ile Phe   181
       CAG GTG TGG TTC GGC CAC CGC TAC TCC CAG TTT ATG GGG ATA TTC
       CAG GTG TGG TTC GGC CAC CGC TAC TCC CAG TTT ATG GGG ATC TTT
       Gln Val Trp Phe Gly His Arg Tyr Ser Gln Phe Met Gly Ile Phe

Glu Asp Arg Ala Pro Val Pro Phe Glu Glu Val Ile Asp Lys Ile
   544 GAG GAC CGC GCC CCC GTT CCC TTC GAG GAG GTG ATC GAC AAG ATT
       GAG GAC CGC GCC CCC GTC CCC TTC GAG GAG GTG ATC GAC AAG ATC
       Glu Asp Arg Ala Pro Val Pro Phe Glu Glu Val Ile Asp Lys Ile

Asn Ala Lys Gly Val Cys Arg Ser Thr Ala Lys Tyr Val Arg Asn   211
       AAC GCC AAG GGG GTC TGC CGC TCC ACG GCC AAG TAC GTG CGG AAC
       AAC GCC AAG GGG GTC TGT CGG TCC ACG GCC AAG TAC GTG CGC AAC
       Asn Ala Lys Gly Val Cys Arg Ser Thr Ala Lys Tyr Val Arg Asn

Asn Met Glu Thr Thr Ala Phe His Arg Asp Asp His Glu Thr Asp
   634 AAC ATG GAG ACC ACC GCG TTT CAC CGG GAC GAC CAC GAG ACC GAC
       AAC CTG GAG ACC ACC GCG TTT CAC CGG GAC GAC CAC GAG ACC GAC
       Asn Leu Glu Thr Thr Ala Phe His Arg Asp Asp His Glu Thr Asp

Met Glu Leu Lys Pro Ala Lys Val Ala Thr Arg Thr Ser Arg Gly   241
       ATG GAG CTC AAG CCG GCG AAG GTC GCC ACG CGC ACG AGC CGG GGG
       ATG GAG CTG AAA CCG GCC AAC GCC GCG ACC CGC ACG AGC CGG GGC
       Met Glu Leu Lys Pro Ala Asn Ala Ala Thr Arg Thr Ser Arg Gly

Trp His Thr Thr Asp Leu Lys Tyr Asn Pro Ser Arg Val Glu Ala
   724 TGG CAC ACC ACC GAC CTC AAG TAC AAC CCC TCG CGG GTG GAG GCG
       TGG CAC ACC ACC GAC CTC AAG TAC AAC CCC TCG CGG GTG GAG GCG
       Trp His Thr Thr Asp Leu Lys Tyr Asn Pro Ser Arg Val Glu Ala

Phe His Arg Tyr Gly Thr Thr Val Asn Cys Ile Val Glu Glu Val   271
       TTC CAT CGG TAC GGC ACG ACG GTC AAC TGC ATC GTC GAG GAG GTG
       TTC CAC CGG TAC GGG ACG ACG GTA AAC TGC ATC GTC GAG GAG GTG
       Phe His Arg Tyr Gly Thr Thr Val Asn Cys Ile Val Glu Glu Val

Asp Ala Arg Ser Val Tyr Pro Tyr Asp Glu Phe Val Leu Ala Thr
   814 GAC GCG CGG TCG GTG TAC CCG TAC GAT GAG TTT GTG TTG GCG ACG
       GAC GCG CGC TCG GTG TAC CCG TAC GAC GAG TTT GTG CTG GCG ACT
       Asp Ala Arg Ser Val Tyr Pro Tyr Asp Glu Phe Val Leu Ala Thr

Gly Asp Phe Val Tyr Met Ser Pro Phe Tyr Gly Tyr Arg Glu Gly   301
       GGC GAC TTT GTG TAC ATG TCC CCG TTT TAC GGC TAC CGG GAG GGG
       GGC GAC TTT GTG TAC ATG TCC CCG TTT TAC GGC TAC CGG GAG GGG
       Gly Asp Phe Val Tyr Met Ser Pro Phe Tyr Gly Tyr Arg Glu Gly
```

FIG. 4B

```
       Ser His Thr Glu His Thr Ser Tyr Ala Ala Asp Arg Phe Lys Gln
 904   TCG CAC ACC GAG CAC ACC AGC TAC GCC GCC GAC CGC TTC AAG CAG
       TCG CAC ACC GAA CAC ACC AGC TAC GCC GCC GAC CGC TTC AAG CAG
       Ser His Thr Glu His Thr Ser Tyr Ala Ala Asp Arg Phe Lys Gln

Val Asp Gly Phe Tyr Ala Arg Asp Leu Thr Thr Lys Ala Arg Ala      331
       GTC GAC GGC TTC TAC GCG CGC GAC CTC ACC ACG AAG GCC CGG GCC
       GTC GAC GGC TTC TAC GCG CGC GAC CTC ACC ACC AAG GCC CGG GCC
       Val Asp Gly Phe Tyr Ala Arg Asp Leu Thr Thr Lys Ala Arg Ala

Thr [Ser] Pro Thr Thr Arg Asn Leu Leu Thr Thr Pro Lys Phe Thr
 994   ACG  TCG  CCG ACG ACC CGC AAC TTG CTG ACG ACC CCC AAG TTT ACC
       ACG  GCG  CCG ACC ACC CGG AAC CTG CTC ACG ACC CCC AAG TTC ACC
       Thr [Ala] Pro Thr Thr Arg Asn Leu Leu Thr Thr Pro Lys Phe Thr

Val Ala Trp Asp Trp Val Pro Lys Arg Pro [Ala] Val Cys Thr Met    361
       GTG GCC TGG GAC TGG GTG CCG AAG CGA CCG  GCG  GTC TGC ACC ATG
       GTG GCC TGG GAC TGG GTG CCA AAG CGC CCG  TCG  GTC TGC ACC ATG
       Val Ala Trp Asp Trp Val Pro Lys Arg Pro [Ser] Val Cys Thr Met

Thr Lys Trp Gln Glu Val Asp Glu Met Leu Arg [Ala] Glu Tyr Gly
1084   ACC AAG TGG CAG GAG GTG GAC GAG ATG CTC CGC  GCC  GAG TAC GGC
       ACC AAG TGG CAG GAG GTG GAC GAG ATG CTG CGC  TCC  GAG TAC GGC
       Thr Lys Trp Gln Glu Val Asp Glu Met Leu Arg [Ser] Glu Tyr Gly

Gly Ser Phe Arg Phe Ser Ser Asp Ala Ile Ser Thr Thr Phe Thr      391
       GGC TCC TTC CGC TTC TCC TCC GAC GCC ATC TCG ACC ACC TTC ACC
       GGC TCC TTC CGA TTC TCC TCC GAC GCC ATA TCC ACC ACC TTC ACC
       Gly Ser Phe Arg Phe Ser Ser Asp Ala Ile Ser Thr Thr Phe Thr

Thr Asn Leu Thr [Gln] Tyr [Ser] Leu Ser Arg Val Asp Leu Gly Asp
1174   ACC AAC CTG ACC  CAG  TAC  TCG  CTC TCG CGC GTC GAC CTG GGC GAC
       ACC AAC CTG ACC  GAG  TAC  CCG  CTC TCG CGC GTT GAC CTG GGG GAC
       Thr Asn Leu Thr [Glu] Tyr [Pro] Leu Ser Arg Val Asp Leu Gly Asp

Cys Ile Gly [Arg] Asp Ala Arg [Glu] Ala [Ile] Asp Arg [Met] Phe Ala  421
       TGC ATT GGC  CGG  GAT GCC CGC  GAG  GCC  ATC  GAC CGC  ATG  TTT GCG
       TGC ATC GGC  AAG  GAC GCC CGC  GAC  GCC  ATG  GAC CGC  ATC  TTC GCC
       Cys Ile Gly [Lys] Asp Ala Arg [Asp] Ala [Met] Asp Arg [Ile] Phe Ala

Arg [Lys] Tyr Asn Ala Thr His Ile Lys Val Gly Gln Pro Gln Tyr
1264   CGC  AAG  TAC AAC GCC ACG CAC ATC AAG GTG GGC CAG CCG CAG TAC
       CGC  AGG  TAC AAC GCG ACG CAC ATC AAG GTC GGC CAG CCG CAG TAC
       Arg [Arg] Tyr Asn Ala Thr His Ile Lys Val Gly Gln Pro Gln Tyr

Tyr Leu Ala [Thr] Gly Gly Phe Leu Ile Ala Tyr Gln Pro Leu Leu    451
       TAC CTG GCC  ACG  GGG GGC TTC CTC ATC GCG TAC CAG CCC CTC CTC
       TAC CTG GCC  AAT  GGG GGC TTT CTG ATC GCG TAC CAG CCC CTT CTC
       Tyr Leu Ala [Asn] Gly Gly Phe Leu Ile Ala Tyr Gln Pro Leu Leu

Ser Asn Thr Leu Ala Glu Leu Tyr Val Arg Glu [Tyr Met] Arg Glu
1354   AGC AAC ACG CTC GCC GAG CTG TAC GTG CGG GAG  TAC ATG  CGG GAG
       AGC AAC ACG CTC GCG GAG CTG TAC GTG CGG GAA  CAC CTC  CGA GAG
       Ser Asn Thr Leu Ala Glu Leu Tyr Val Arg Glu [His Leu] Arg Glu

Gln [Asp] Arg Lys Pro [Arg] Asn [Ala] Thr Pro [Ala] Pro [Leu Arg Glu]  481
       CAG  GAC  CGC AAG CCC  CGG  AAT  GCC  ACG CCC  GCG  CCA  CTG CGG GAG
       CAG  AGC  CGC AAG CCC  CCA  ACC  CCC  ACG CCC  CCG  CCG  CCC ::: :::
       Gln [Ser] Arg Lys Pro [Pro] Asn [Pro] Thr Pro [Pro] Pro  Pro
```

FIG. 4C

```
     Ala Pro Ser Ala Asn Ala Ser Val Glu Arg Ile Lys Thr Thr Ser
1444 GCG CCC AGC GCC AAC GCG TCC GTG GAG CGC ATC AAG ACC ACC TCC
     GGG GCC AGC GCC AAC GCG TCC GTG GAG CGC ATC AAG ACC ACC TCC
     Gly Ala Ser Ala Asn Ala Ser Val Glu Arg Ile Lys Thr Thr Ser

Ser Ile Glu Phe Ala Arg Leu Gln Phe Thr Tyr Asn His Ile Gln  511
     TCG ATC GAG TTC GCC CGG CTG CAG TTT ACG TAT AAC CAC ATA CAG
     TCC ATC GAG TTC GCC CGG CTG CAG TTT ACG TAC AAC CAC ATA CAG
     Ser Ile Glu Phe Ala Arg Leu Gln Phe Thr Tyr Asn His Ile Gln

Arg His Val Asn Asp Met Leu Gly Arg Ile Ala Val Ala Trp Cys
1534 CGC CAC GTG AAC GAC ATG CTG GGG CGC ATC GCC GTC GCG TGG TGC
     CGC CAT GTC AAC GAT ATG TTG GGC CGC GTT GCC ATC GCG TGG TGC
     Arg His Val Asn Asp Met Leu Gly Arg Val Ala Ile Ala Trp Cys

Glu Leu Gln Asn His Glu Leu Thr Leu Trp Asn Glu Ala Arg Lys  541
     GAG CTG CAG AAC CAC GAG CTG ACT CTC TGG AAC GAG GCC CGC AAG
     GAG CTG CAG AAC CAC GAG CTG ACC CTG TGG ACC GAG GCC CGC AAG
     Glu Leu Gln Asn His Glu Leu Thr Leu Trp Asn Glu Ala Arg Lys

Leu Asn Pro Asn Ala Ile Ala Ser Ala Thr Val Gly Arg Arg Val
1624 CTC AAC CCC AAC GCC ATC GCC TCC GCC ACC GTC GGC CGG CGG GTG
     CTG AAC CCC AAC GCC ATC GCC TCG GCC ACC GTG GGC CGG CGG GTG
     Leu Asn Pro Asn Ala Ile Ala Ser Ala Thr Val Gly Arg Arg Val

Ser Ala Arg Met Leu Gly Asp Val Met Ala Val Ser Thr Cys Val  571
     AGC GCG CGC ATG CTC GGA GAC GTC ATG GCC GTC TCC ACG TGC GTG
     AGC GCG CGG ATG CTC GGC GAC GTG ATG GCC GTC TCC ACG TGC GTG
     Ser Ala Arg Met Leu Gly Asp Val Met Ala Val Ser Thr Cys Val

Pro Val Ala Pro Asp Asn Val Ile Val Gln Asn Ser Met Arg Val
1714 CCC GTC GCC CCG GAC AAC GTG ATC GTG CAG AAC TCG ATG CGC GTC
     CCG GTC GCC GCG GAC AAC GTG ATC GTC CAA AAC TCG ATG CGC ATC
     Pro Val Ala Ala Asp Asn Val Ile Val Gln Asn Ser Met Arg Ile

Ser Ser Arg Pro Gly Thr Cys Tyr Ser Arg Pro Leu Val Ser Phe  601
     AGC TCG CGG CCG GGG ACG TGC TAC AGC CGC CCC CTG GTC AGC TTT
     AGC TCG CGG CCC GGG GCC TGC TAC AGC CGC CCC CTG GTC AGC TTT
     Ser Ser Arg Pro Gly Ala Cys Tyr Ser Arg Pro Leu Val Ser Phe

Arg Tyr Glu Asp Gln Gly Pro Leu Ile Glu Gly Gln Leu Gly Glu
1804 CGG TAC GAA GAC CAG GGC CCG CTG ATC GAG GGG CAG CTG GGC GAG
     CGG TAC GAA GAC CAG GGC CCG TTG GTC GAG GGG CAG CTG GGG GAG
     Arg Tyr Glu Asp Gln Gly Pro Leu Val Glu Gly Gln Leu Gly Glu

Asn Asn Glu Leu Arg Leu Thr Arg Asp Ala Leu Glu Pro Cys Thr  631
     AAC AAC GAG CTG CGC CTC ACC CGC GAC GCG CTC GAG CCG TGC ACC
     AAC AAC GAG CTG CGG CTG ACG CGC GAT GCG ATC GAG CCG TGC ACC
     Asn Asn Glu Leu Arg Leu Thr Arg Asp Ala Ile Glu Pro Cys Thr

Val Gly His Arg Arg Tyr Phe Ile Phe Gly Gly Gly Tyr Val Tyr
1894 GTG GGC CAC CGG CGC TAC TTC ATC TTC GGC GGG GGC TAC GTG TAC
     GTG GGA CAC CGG CGC TAC TTC ACC TTC GGT GGG GGC TAC GTG TAC
     Val Gly His Arg Arg Tyr Phe Thr Phe Gly Gly Gly Tyr Val Tyr

Phe Glu Glu Tyr Ala Tyr Ser His Gln Leu Ser Arg Ala Asp Val  661
     TTC GAG GAG TAC GCG TAC TCT CAC CAG CTG AGT CGC GCC GAC GTC
     TTC GAG GAG TCA GCG TAC TCC CAC CAG CTG AGC CGC GCC GAC ATC
     Phe Glu Glu Ser Ala Tyr Ser His Gln Leu Ser Arg Ala Asp Ile
```

FIG.4D

```
        Thr Thr Val Ser Thr Phe Ile Asp Leu Asn Ile Thr Met Leu Glu
1984    ACC ACC GTC AGC ACC TTC ATC GAC CTG AAC ATC ACC ATG CTG GAG
        ACC ACC GTC AGC ACC TTC ATC GAC CTC AAC ATC ACC ATG CTG GAG
        Thr Thr Val Ser Thr Phe Ile Asp Leu Asn Ile Thr Met Leu Glu

Asp His Glu Phe Val Pro Leu Glu Val Tyr Thr Arg His Glu Ile   691
        GAC CAC GAG TTT GTG CCC CTG GAG GTC TAC ACG CGC CAC GAG ATC
        GAT CAC GAG TTT GTC CCC CTG GAG GTG TAC ACC CGC CAC GAG ATC
        Asp His Glu Phe Val Pro Leu Glu Val Tyr Thr Arg His Glu Ile

Lys Asp Ser Gly Leu Leu Asp Tyr Thr Glu Val Gln Arg Arg Asn
2074    AAG GAC AGC GGC CTG CTG GAC TAC ACG GAG GTC CAG CGC CGC AAC
        AAG GAC AGC GGC CTG CTG GAC TAC ACG GAG GTC CAG CGC CGC AAC
        Lys Asp Ser Gly Leu Leu Asp Tyr Thr Glu Val Gln Arg Arg Asn

Gln Leu His Asp Leu Arg Phe Ala Asp Ile Asp Thr Val Ile |Arg|  721
        CAG CTG CAC GAC CTG CGC TTT GCC GAC ATC GAC ACG GTC ATC |CGC|
        CAG CTG CAC GAC CTG CGC TTC GCC GAC ATC GAC ACG GTC ATC |CAC|
        Gln Leu His Asp Leu Arg Phe Ala Asp Ile Asp Thr Val Ile |His|

Ala Asp Ala Asn Ala Ala Met Phe Ala Gly Leu |Cys| Ala Phe Phe
2164    GCC GAC GCC AAC GCC GCC ATG TTC GCG GGG CTG |TGC| GCG TTC TTC
        GCC GAC GCC AAC GCC GCC ATG TTC GCG GGC CTG |GGT| GCG TTT TTC
        Ala Asp Ala Asn Ala Ala Met Phe Ala Gly Leu |Gly| Ala Phe Phe

Glu Gly Met Gly Asp Leu Gly Arg Ala Val Gly Lys Val Val Met   751
        GAG GGG ATG GGG GAC TTG GGG CGC GCG GTC GGC AAG GTA GTC ATG
        GAG GGG ATG GGC GAC CTG GGG CGC GCG GTC GGC AAG GTG GTG ATG
        Glu Gly Met Gly Asp Leu Gly Arg Ala Val Gly Lys Val Val Met

Gly |Val| Val Gly Gly Val Val Ser Ala Val Ser Gly Val Ser Ser
2254    GGA |GTA| GTG GGG GGC GTG GTG TCG GCC GTC TCG GGC GTG TCC TCC
        GGC |ATC| GTG GGC GGC GTG GTA TCG GCC GTG TCG GGC GTG TCC TCC
        Gly |Ile| Val Gly Gly Val Val Ser Ala Val Ser Gly Val Ser Ser

Phe Met Ser Asn Pro Phe Gly Ala Leu Ala Val Gly Leu Leu Val
        TTT ATG TCC AAC CCC TTC GGG GCG CTT GCC GTG GGG CTG CTG GTC
        TTC ATG TCC AAC CCC TTT GGG GCG CTG GCC GTG GGT CTG TTG GTC
        Phe Met Ser Asn Pro Phe Gly Ala Leu Ala Val Gly Leu Leu Val

Leu Ala Gly Leu |Val| Ala Ala Phe Phe Ala Phe Arg Tyr Val |Leu|
2344    CTG GCC GGC CTG |GTC| GCG GCC TTC TTC GCC TTC CGC TAC GTC |CTG|
        CTG GCC GGC CTG |GCG| GCG GCC TTC TTC GCC TTT CGC TAC GTC |ATG|
        Leu Ala Gly Leu |Ala| Ala Ala Phe Phe Ala Phe Arg Tyr Val |Met|

Gln Leu Gln |Arg| Asn Pro Met Lys Ala Leu Tyr Pro Leu Thr Thr  811
        CAA CTG CAA |CGC| AAT CCC ATG AAG GCC CTG TAT CCG CTC ACC ACC
        CGG CTG CAG |AGC| AAC CCC ATG AAG GCC CTG TAC CCG CTA ACC ACC
        |Arg| Leu Gln |Ser| Asn Pro Met Lys Ala Leu Tyr Pro Leu Thr Thr

Lys Glu Leu Lys |Thr Ser Asp Pro Gly Gly Val Gly| Gly Glu Gly
2434    AAG GAA CTC AAG |ACT TCC GAC CCC GGG GGC GTG GGC| GGG GAG GGG
        AAG GAG CTC AAG |AAC CCC ACC AAC CCG GAC GCG TCC| GGG GAG GGC
        Lys Glu Leu Lys |Asn Pro Thr Asn Pro Asp Ala Ser| Gly Glu Gly

Glu Glu Gly |Ala Glu Gly|Gly |Gly|Phe Asp Glu Ala Lys Leu Ala   841
        GAG GAA GGC |GCG GAG GGG|GGC |GGG|TTT GAC GAG GCC AAG TTG GCC
        GAG GAG GGC |::: ::: :::|GGC |GAC|TTT GAC GAG GCC AAG CTA GCC
        Glu Glu Gly |           |Gly |Asp|Phe Asp Glu Ala Lys Leu Ala
```

FIG. 4E

```
         Glu Ala Arg Glu Met Ile Arg Tyr Met Ala Leu Val Ser Ala Met
    2524 GAG GCC CGA GAA ATG ATC CGA TAT ATG GCT TTG GTG TCG GCC ATG
         GAG GCC CGG GAG ATG ATA CGG TAC ATG GCC CTG GTG TCT GCC ATG
         Glu Ala Arg Glu Met Ile Arg Tyr Met Ala Leu Val Ser Ala Met

Glu Arg Thr Glu His Lys Ala Arg Lys Lys Gly Thr Ser Ala Leu    871
         GAG CGC ACG GAA CAC AAG GCC AGA AAG AAG GGC ACG AGC GCC CTG
         GAG CGC ACG GAA CAC AAG GCC AAG AAG AAG GGC ACG AGC GCG CTG
         Glu Arg Thr Glu His Lys Ala Lys Lys Lys Gly Thr Ser Ala Leu

Leu Ser Ser Lys Val Thr Asn Met Val Leu Arg Lys Arg Asn Lys
    2614 CTC AGC TCC AAG GTC ACC AAC ATG GTT CTG GCC AAG CGC AAC AAA
         CTC AGC GCC AAG GTC ACC GAC ATG GTC ATG CGC AAG CGC CGC AAC
         Leu Ser Ala Lys Val Thr Asp Met Val Met Arg Lys Arg Arg Asn

Ala Arg Tyr Ser Pro Leu His Asn Glu Asp Glu Ala Gly Asp Glu    901
         GCC AGG TAC TCT CCG CTC CAC AAC GAG GAC GAG GCC GGA GAC GAA
         ACC AAC TAC ACC CAA GTT CCC AAC AAA GAC GGT GAC GCC GAC GAG
         Thr Asn Tyr Thr Gln Val Pro Asn Lys Asp Gly Asp Ala Asp Glu

Asp Glu Leu OC
    2704 GAC GAG CTC TAA GGGAGGGGAGGGGAGCTGGGCTTGTGTATAAATAAAAAGACACC
         GAC GAC CTG TGA CGGGGGGTTTGTTGTAAATAAAAACCACGGGTGTTAAACCGCAT
         Asp Asp Leu OP
                                                                        904
         GATGTTCAAAAATACACATGACTTCTGGTATTGTTTTGCCTTGGTTTTTATTTGGGGGG
         GTGCATCTTTTGGTGTGTTTGTTTGGTACGCCTTTTGTGTGTGTGGGAAGAAAGAAAAG

2819 GGGGCGTGTGACTAGAAAAACAAATGCAGACATGTGCTAACGGGAAAACCAACCCCAAAC
         GGAACACATAAACTCCCCCGGGTGTCCGCGGCCTGTTTCCTCTTTCCTTTCCCGTGACAA

CAACCCCAAACCAACCCCGTCTCCCTGCGACCGGTCGCTTTCCACACCCCCTCCCCGTG
         AACGGACCCCCTTGGTCAGTGCCGATTCCCCCCCACGCCTTCCTCCACGTCGAAGGCTT

2938 GTAGTCTTCCGGGCCTTCCGTCGCGTGTGGGGGCCATCGGTTCGGCTCCTAGCCCCCCCC
         TTGCATTGTAAAGCTACCCGCCTACCCGCGCCTCCCAATAAAAAAAAAGAACATACACCA

CCCTCACCCCTCCGACCTAATTTTTGTGTCATTCGGCCCACTTTCCCCCCCACTCCACC
         ATGGGTCTTATTTGGTATTACCTGGTTTATTTAAAAAGATATACAGTAAGACATCCCAT

3057 CCCCCCCTCTCAAACAAAAACACAAGCACACGAAGTGGGTATACTTTTGTCCGGTTGTTT
         GGTACCAAAGACCGGGGCGAATCAGCGGGCCCCCATCATCTGAGAGACGAACAAATCGGC

GTTTATTTAAAATATATGAAAACACACACCCCCCCCAAGTCCGGATCC
         GGCGCGGGCCGTGTCAACGTCCACGTGTGCTGCGCTGCTGGCGTTGAC
```

FIG.4F

DNA a

```
         10         20         30         40         50         60
  0 CTCGAGAAGA TGCTGCGGGT CAGCGTCCAC GGCGAGGTGC TGCCCGCCGA CCTCTCGCCG
         70         80         90        100        110        119
 60 CGGTCGCCAA CGGCTTCGCG GCGCGCGCGC GCTTCTGCGC CCTGACGGCG GGCGCGGGC
```

DNA b

```
206 CTGCAGCCGCCCGACCTCCGAAG TCGTTACCGTTACCCGCCCGGCGTATATCTCACGTACGACTCCGACTG
    ******************** ** ***** ******** ***** ** ******** **********
  1 CTGCAGCCGCCCGACCTCCGAAGGTCTGTACCGCTACCCGCCGGGCGTGTACCTCACGTACAACTCCGACTG

278 TCCGCTGGTGGCCATCGTCGAGAGCGCCCCCGACGGCTGTATCGGCCCCCGGTCGGTCGTGGTCTACGACCG
    ************************* ************ ***** ***** ********** ********
 73 TCCGCTGGTGGCCATCGTCGAGAGCGGCCCCGACGGCTGCATCGGACCCCGCTCGGTCGTGGTTTACGACCG

350 AGACGTTTTCTCGATCCTCTACTCGGTCCTCCAGCACCTCGCCCCCAGGCTACCTGACGGGGGGCACGACGG
    ********* **  ******** **********  ***
145 AGACGTTTTTTCCATCCTCTACTCGGTCCTGCAG
```

DNA c

```
285 TGGCCATCGTCG AGAGCGCCCCCGACGGCTGTATCGGCCCCCGGTCGGTCGTGGTCTACGACCGAGACGTT
    ***********  ***** ***** ********** ********* ***** ********** ********
  1 TGGCCATCGTCGCAGAGCGGCCCCGACGGCTGCATCGGACCCCGCTCGGTCGTGGTTTACGACCGAGACGTT

357 TTCTCGATCCTCTAC TCGGTCCTCCAGCACCTCGCCCCCAGGCTACCTGACGGGGGGCACGACGGGCCCCC
    ** ** *********  ********* ******************* *** * *** ***   ** ******
 73 TTTTCCATCCTCTACCTCGGTCCTGCAGCACCTCGCCCCCAGACTAGCGGGCGGCGGGAGGCACCGGCCCCG

429 GTAGTCCCGCCATGCGCCAGGGCGCCCCCGCGCGGGGGTGCCGGTGGTTCGTCGTATGGGCGCTCTTGGGGT
    ***  ********* **  *     * *    ***  *   *   ***    *  * *
145  TAG CCCGCCATGCGCGGGGGGGGGCTTGATTTGCGCGCTGGTCGTGGGGGCGCTGGTGGCCGCGGTCGGCG

501 TGACGCTGGGGGTCCTGGTGGCGTCGGCGGCTCCGAGTTCCCCCGGCACGCCTGGGGTCGCGGCCGCGACCC
    *  ***
217 TCGCGCCC
```

FIG.9A

DNA d

```
 888 AAGGAGAACATCGCCCCGTACAAGTTCAAGGCCACCATGTACTACAAAGACGTCACCGTT TCGCAGGTGTG
     ******************* *** ****************************** *** **********
   1 AAGGAGAACATCGCCCCGATCAAATTCAAGGCCACCATGTACTACAAAGACGTGACCTGGGTCGCAGGTGTG

960 GTTCGGCCACCGCTACTCCCAGTTTATGGGGATCTTTGAGGACCGCGCCCCCGTCCCCTTCGAGGAGGTGAT
     ******************************* ** ***************** ****************
  73 GTTCGGCCACCGCTACTCCCAGTTTATGGGGATATTCCAGGACCGCGCCCCCGTTCCCTTCGAGGAGGTGAT

1032 CGACAAGATC AACGCCAAGGGGGTCTGTCGGTCCACGGCCAAGTACGTGCGCAACAACCTGGAGACCACCG
     *******    ************* ** * ****************** ****** ** ************
 145 CGACAAGCATTAACGCCAAGGGGG CTCTGCCTCCACGGCCAAGTACGTCCGGAACAACATGGAGACCACCG

1104 CGTTTCACCGGGACGACCACGAGACCGACATGGAGCTGAAACCGGCCAACGCCCGCGACCCGCACGAGCCGG
     ************************************** ** ***** ** *  *** ** ***********
 217 CGTTTCACCGGGACGACCACGAGACCGACATGGAGCTCAAGCCGGCGAAGGT CGCCACGCGCACGAGCCGG

1176 GGCTGGCACACCACCGACCTCAAGTACAACCCCTCGCGGGTGGAGGCGTTCCACCGGTACGG ACGACGGTA
     ** ************************* ************************ ******** ********
 289 GGGTGGCACACCACCGACCTCAAGTACAACC TCGCGGGTGGAGGCGTTCCATCGGTACGGCACGACGGTC
```

DNA e

```
1950 CTGCAGTTTACGTACAACCACATACAGCGCCATGTCAACGATATGTTGGGCCGCGTTGCCATCGCCTGGTGC
     ***************** ****************** ***** *** **** * *** ***********
   1 CTGCAGTTTACGTATAACCACATACAGCGCCACGTGAACGACATGCTGGGGCGCATCGCCGTCGCGTGGTGC

2022 GAGCTGCAGAATCACAAGCTGACCCTGTGGAACGAGGCCCGCAAGCTGAACCCCAACGCCATCGCCTCGGCC
     *********
  73 GAGCTGCAG
```

DNA f

```
2276 GGGGCAGCTGGGGGAGAACAACGAGCTGCGGCTGACGCGCGATGCGATCGAGCCGTGCACCGTGGGACACCG
     ************ ****************** ** *****   **
   1 GGGGCAGCTGGGCGAGAACAACGAGCTGCGCCTCACGCGACGCGC
```

FIG. 9B

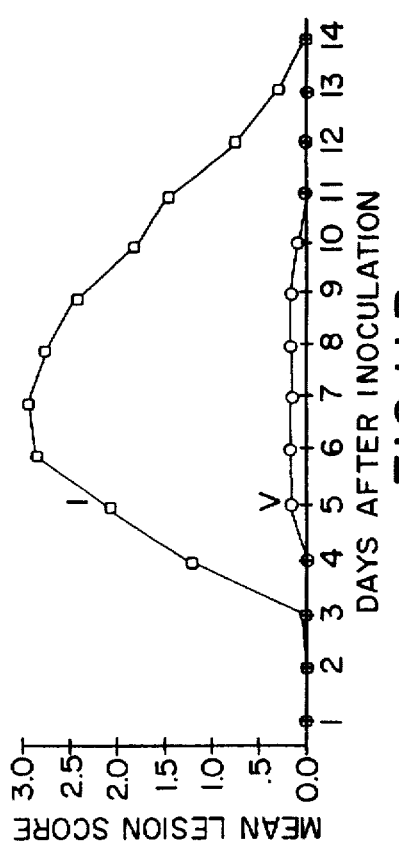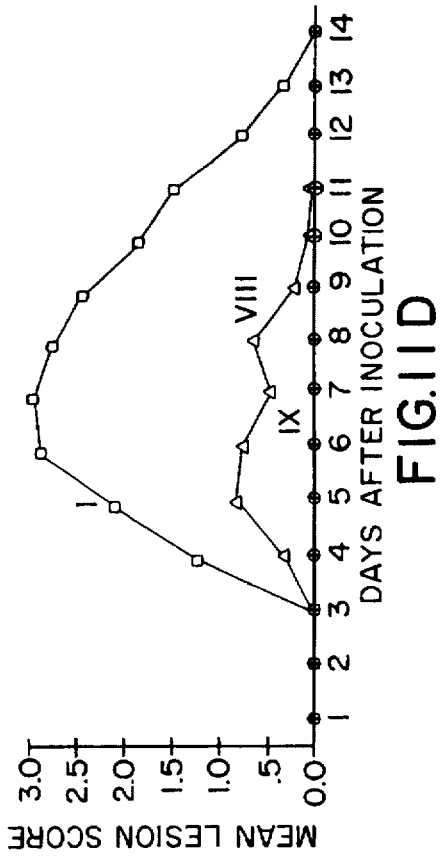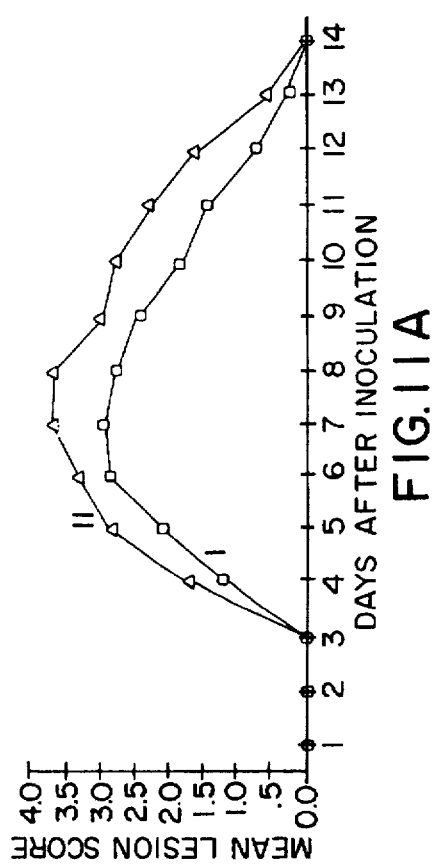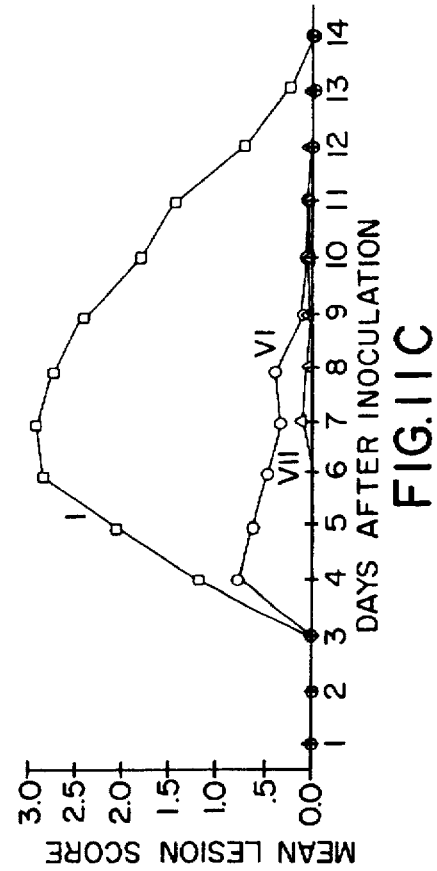

EXPRESSION OF RECOMBINANT GLYCOPROTEIN B FROM HERPES SIMPLEX VIRUS

CROSS-REFERENCE TO RELATED APPLICATIONS

This application is a division of U.S. application Ser. No. 08/351,875, filed Dec. 8, 1994, now U.S. Pat. No. 5,648,079, which is a continuation of U.S. application Ser. No. 08/138, 717, filed Oct. 18, 1993, abandoned, which is a continuation of U.S. application Ser. No. 07/993,415, filed Dec. 21, 1992, abandoned, which is a division of U.S. application Ser. No. 07/587179, filed Sep. 20, 1990, now U.S. Pat. No. 5,244, 792, which is a continuation of U.S. application Ser. No. 06/921,730, filed Oct. 20, 1986, abandoned, which is a continuation in part of U.S. application Ser. No. 06/597,784, filed Apr. 06, 1984, abandoned.

BACKGROUND OF THE INVENTION FIELD OF THE INVENTION

The herpes viruses include the Herpes Simplex virus, (HSV), comprising two closely related variants designated types 1 (HSV-1) and 2 (HSV-2). These types cross react strongly but can be distinguished by neutralization titrations. HSV-1 and HSV-2 are responsible for a variety of human diseases, such as skin infections, genital herpes, viral encephalitis and the like.

HSV is a double-stranded DNA virus having a genome of about 150 to 160 kbp packaged within an icosahedral nucleocapsid enveloped in a membrane. The membrane includes a number of virus-specific glycoproteins, the most abundant of which are gB, gC, gD and gE, where gB and gD are cross-reactive between types 1 and 2.

It is a matter of great medical and scientific interest to provide safe and effective human vaccines against both HSV-1 and HSV-2 and, where infection has occurred, therapies for treatment of the disease.

One promising approach to the production of human vaccines against HSV has been the use of isolated glycoproteins, which have been shown to provide protection when injected into mice subsequently challenged with live virus. However, the availability of the Herpes Simplex glycoproteins has heretofore been primarily dependent upon the growth of the virus and the isolation of the membranous proteins. The problems of commercial production of the glycoproteins associated with the handling of a dangerous pathogen, the maintenance of the virus in cell culture, the isolation of the glycoproteins free of the viral genome or portions thereof, have substantially precluded the use of the glycoproteins as vaccines. It would therefore be desirable to provide human vaccines employing glycoproteins produced by methods other than by growth of the virus and isolation of the membranes proteins.

DESCRIPTION OF THE RELEVANT LITERATURE

Eberle and Mou, *J. of Infectious Diseases* (1983) 148:436–444, report the relative titers of antibodies to individual polypeptide antigens of HSV-1 in human sera. Marsden et al., *J. of Virology* (1978) 28:624–642, report the location of a gene for a 117 kilodalton (kd) glycoprotein to lie within 0.35–0.40 map units on the genetic map of HSV by intertypic recombination between HSV-1 and HSV-2. Ruyechan et al., ibid. (1979) 29:677–697, also report the mapping of glycoprotein B gene to lie between 0.30–0.42 map units. Skare and Summers, *Virology* (1977) 76:581–595, report endonuclease cleavage sites for EcoRI. XbaI and HindIII on HSV-1 DNA. Roizman, *Ann. Rev. Genetics* (1979) 13:25–57, reports the organization of the HSV genomes. DeLucca et al., *Virology* (1982) 122:411, map several phenotypic mutants thought to lie in the gB1 structural gene between 0.345 to 0.368 map units.

Subunit vaccines extracted from chick embryo cells infected with HSV-1 or HSV-2 are described in U.S. Pat. Nos. 4,317,811 and 4,374,127. See also, Hilfenhaus et al., *Develop. Biol. Standard* (1982) 52:287–304, describe the preparation of nonvirulent HSV-1×HSV-2 recombinants and deletion mutants which are shown to be effective in immunizing mice. Weis et al., Nature (1983) 302:72–74 report that gD elicits neutralizing antibodies in rabbits. Lasky et al., *Biotechnology* (June 1984) 527–532, report the use of this glycoprotein D for the immunization of mice. Berman et al. *Science* (1985) 227:1490–1492, report the use of recombinant glycoprotein D for the immunization of guinea pigs.

"Therapeutic" use of preparations of membrane proteins from HSV-infected cells for post-infection vaccine in humans are reported by Cappel et al., J. Medical Virol. (1985) 16:137–145; Dundarov, S. et al., Dev. Biol. Standard (1982) 52:351–357; and Skinner, G. R. B. et al., ibid. (1982) 52:333–34.

SUMMARY OF THE INVENTION

The nucleotide sequence and the amino acid sequence derived therefrom are provided for Herpes Simplex Virus ("HSV") glycoprotein B ("gB") for use in expression of the glycoprotein, synthesis of constructs for expression, production of the glycoprotein, use of the glycoprotein in vaccines, and use of the nucleotide fragments in the aforementioned constructions and as probes. Particularly, DNA was identified as coding for gB and was manipulated with expression vectors for expression in eukaryotic cells. The precursor and mature gB proteins and portions thereof are provided free of HSV genomic DNA. Vaccines containing gB protein as well as methods for preparing and using the vaccines are also provided.

Accordingly, one aspect of the invention provides a DNA construct which contains an oligonucleotide sequence substantially free of natural flanking regions, which encodes a polypeptide similar to glycoprotein B of HSV or its functional fragments. The DNA construct also contains transcriptional and translational regulatory sequences flanking the oligonucleotide sequence; at least one of these regulatory sequences is other than an HSV regulatory sequence. In addition, the construct contains sequences which allow for its expression in a eukaryotic system.

Another aspect of the invention provides a eukaryotic host harboring the expression construct as well as a system which allows for replication of the construct, which is joined to the construct.

Another aspect of the invention provides a vaccine which contains a recombinant polypeptide which is immunologically cross reactive with glycoprotein B of HSV. The polypeptide is present in an amount effective to produce an immune response in a mammalian host. The polypeptide is synthesized via the expression of the DNA construct described above.

Another aspect of the invention provides a method for preparing vaccines against herpes simplex virus. In this method an immunologically active polypeptide which is cross-reactive with glycoprotein B of HSV is synthesized in a eukaryotic host. The polypeptide is isolated. A vaccine is formulated using an immunogenic amount of the polypeptide and a pharmacologically acceptable carrier.

Another aspect of the invention provides for the immunization of a mammal against HSV by vaccination of the mammal with the above described vaccine.

BRIEF DESCRIPTION OF THE DRAWINGS

FIG. 4 shows the DNA sequences and corresponding deduced amino acid sequences of gB1 and gB2.

FIG. 9 shows the DNA sequences for the fragments derived from gB2 DNA inserted in pHS203.

FIG. 11 is a graph showing the effect of vaccines on the clinical course of external genical skin disease in female guinea pigs intravaginally inoculated with HSV-2.

DESCRIPTION OF THE SPECIFIC EMBODIMENTS

Figure 1:
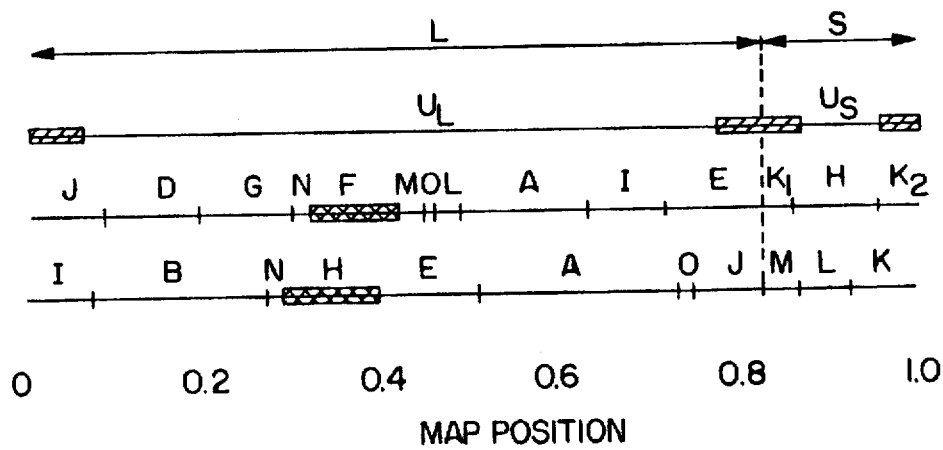
FIG. 1 shows physical maps of HSV-1 and HSV-2, and EcoRI, and HindIII restriction maps of RSV-1 and HSV-2, respectively.

Recombinant Herpes Simples Virus glycoprotein B (gB) of both Types 1 and 2 are provided, including fragments, precursors and analogs, as well as DNA sequences encoding for the precursors and the mature amino acid sequence and fragments thereof. In addition, constructs are provided for the eukaryotic expression of gB in both microorganism and mammalian cells.

FIG. 4 in the Experimental section provides the nucleotide sequences for gB1 strain Patton and gB2 strain 333, as well as the amino acid sequences encoded therein. This figure also shows the substantial homology between gB1 and gB2. The nucleotide sequences for a gB may be varied in numerous ways. Fragments encoding portions of the gB polypeptide, when these portions have independent functions, may be joined to those encoding proteins other than the mature gB. In addition, the various codons may be modified so as the encode for the same amino acids, but provide more efficient expression in accordance with the nature of the host. For example, the codons may be modified in accordance with the frequency of occurrence of a particular codon in one or more proteins or groups of proteins, e.g., glycolytic proteins, which contribute to a high proportion of the total proteins of a particular host, e.g., yeast. In some instances one or more codons may be modified to code for a different amino acid, substituting one amino acid for another amino acid, where the effect of the change is not detrimental to the immunogenicity of the protein or to other biological factors of interest. Such changes may be made to enhance the immunogenicity of the polypeptide, facilitate conjugating the polypeptide to a carrier protein, or the like. It may be desirable in some instances to add amino acids to the N-terminus or C-terminus, where such additional amino acids may provide-for a desired result. This can be readily achieved by providing for additional codons at the 5'- or 3'- termini of the sequence encoding the mature gB or its precursor.

While the amino acid sequence of gB2 may differ from that of gB1 by as much as 20 number percent, other strains of HV-1 or of HSV-2 will have gB glycoproteins the same as or similar to gB1 strain Patton or gB2 strain 333, respectively, usually differing by fewer than 5 number percent, more usually differing by fewer than 2 number percent, and frequently differing by fewer than 0.5 number percent amino acids from the amino acid sequence of gB1 strain Patton or gB2 strain 333.

The gB1 sequence, particularly gB1 strain Patton, may be divided into four domains beginning at the N-terminus of the protein: a first hydrophobic region extending from amino acid 1 to about amino acid 30; a region of variable polarity extending from the first hydrophobic region to about amino acid 726; a second hydrophobic region extending from said variable polarity region to about amino acid 795; and a second variable polarity region extending to the C-terminus at amino acid 904.

Since gB is a membrane glycoprotein, based on analogy with other glycoproteins, the first hydrophobic region may be considered the signal leader sequence directing secretion and/or membrane location. The first sequence of variable polarity would then be external to the membrane and serve as the recognition sequence, to the extent that gB serves as a receptor for another protein or as an immunogen in a vaccine. The second hydrophobic sequence may serve as a transmembrane integrator sequence (often termed the "anchor"), which can be joined to other amino acid sequences to bind them to a membrane. The second variable polarity amino acid sequence would be expected to be in the cytoplasm and, to the extent that a receptor is external to the transmembrane integrator sequence, may serve to modulate one or more cytoplasmic processes.

Each of the above sequences may have individual utility as well as utility combined with the other sequences. The first hydrophobic sequence can serve as a signal leader sequence and be joined to DNA sequences coding for unnatural amino acid sequences to provide for transfer from the endoplasmic reticulum through the external membrane, with loss of the signal leader. (By "unnatural" is intended a sequence other than the naturally occurring sequence associated with an indicated flanking sequence.) In this manner, various proteins, particularly those produced in mammalian host cells, can be modified with the signal leader sequence, so as to be secreted from the host cell. The first variable polar region can serve as an immunogen for the production of antibodies capable of neutralizing HSV, as a competitive inhibitor for infection, as a reagent in immunoassays, either labeled or unlabeled, for the detection of antibodies specific for gB, or the like; the second hydrophobic region can serve to bind a protein, i.e., "anchor" it, to a membrane. Thus, this region can be joined to unnatural proteins, so as to maintain the proteins bound to the membrane. By employing hybrid DNA technology, one can produce a wide variety of surface membrane proteins different from the naturally occurring surface membrane proteins. By inserting an unnatural polynucleotide sequence between the first and second hydrophobic regions, and expressing the hybrid polynucleotide in an appropriate host, the unnatural protein can be provided on the surface of the cell. Thus, cells can be modified as to their binding characteristics for use as reagents in assays, to modify their growth patterns, to act as competitive activators or inhibitors in vivo, and the like. Finally, the second hydrophobic region can be used in conjunction with the transmembrane integrator sequence and sequences encoding an unnatural polypeptide, where such polypeptide can serve as a receptor and actuate the second variable region to initiate a physiological effect in a host cell. In this manner, cells can be modified to respond to different ligands, as if binding was occurring to the gB protein.

The polynucleotide sequence encoding for the precursor to gB or functional fragments thereof may be cloned and expressed by inserting the polynucleotide sequence into an appropriate expression vector and introducing the resulting expression product construct into a compatible host. The coding fragments will be less than about 0.1 map unit, usually less than about 0.05 map unit where 1.0 map unit is the size of the entire HSV genome. The expression vector may be a low or high multicopy vector which exists extra-chromosomally or integrated into the genome of the host cell and may provide for secretion or excretion of the polypeptide of interest or retention of the polypeptide of interest in the cytoplasm or in the membrane. A large number of cloning and expression vectors have been published in the literature and are generally available for use in either prokaryotic or eukaryotic hosts, including bacteria, e.g., *E. coli.*, *B. subtilis*, etc., fungi, particularly yeast, e.g., *S. cerevisiae*, and a wide variety of immortalized mammalian cells, such as mouse cells, monkey cells, hamster cells, e.g., 3T3, Vero, Chinese Hamster Ovary cells (CHO), etc., as well as primary cell lines. Depending upon the host, where secretion is desired, either the native or unnatural secretory leader sequence may be employed. The processing signals for cleavage of the secretory leader may be the natural signals or the signals associated with the unnatural secretory leader or both in tandem.

For secretion, the polynucleotide sequence will require the first hydrophobic region, while being free of the second hydrophobic region and normally the second variable polar region. For retention in the cytoplasm, the polynucleotide sequence will be free of the sequence coding the secretory leader sequence and may or may not have the second hydrophobic sequence including the second variable polar region. To remove the individual functional sequences or to join a particular functional sequence to an unnatural sequence, the polynucleotide sequence encoding the gB precursor can be restriction mapped, and where appropriate restriction sites are found, the sequence may be cleaved at or near the desired site or the desired site may be engineered into the sequence by in vitro mutagenesis or substitution of a chemically synthesized fragment. Where excess nucleotides exist, these can be removed by resection, for example, with Bal31 or where the sequence has been truncated, the lost nucleotides may be replaced by employing chemically synthesized adapters. By appropriate choice of adapters, restriction sequences may be maintained and/or new restriction sequences introduced. In some instances, it may be useful to fill in the overhand resulting from restriction employing the Klenow fragment to provide for blunt ends, followed by blunt-end ligation with an appropriate ligase. Selection may then be made for the hybrid DNA having the appropriate orientation.

Figure 2:
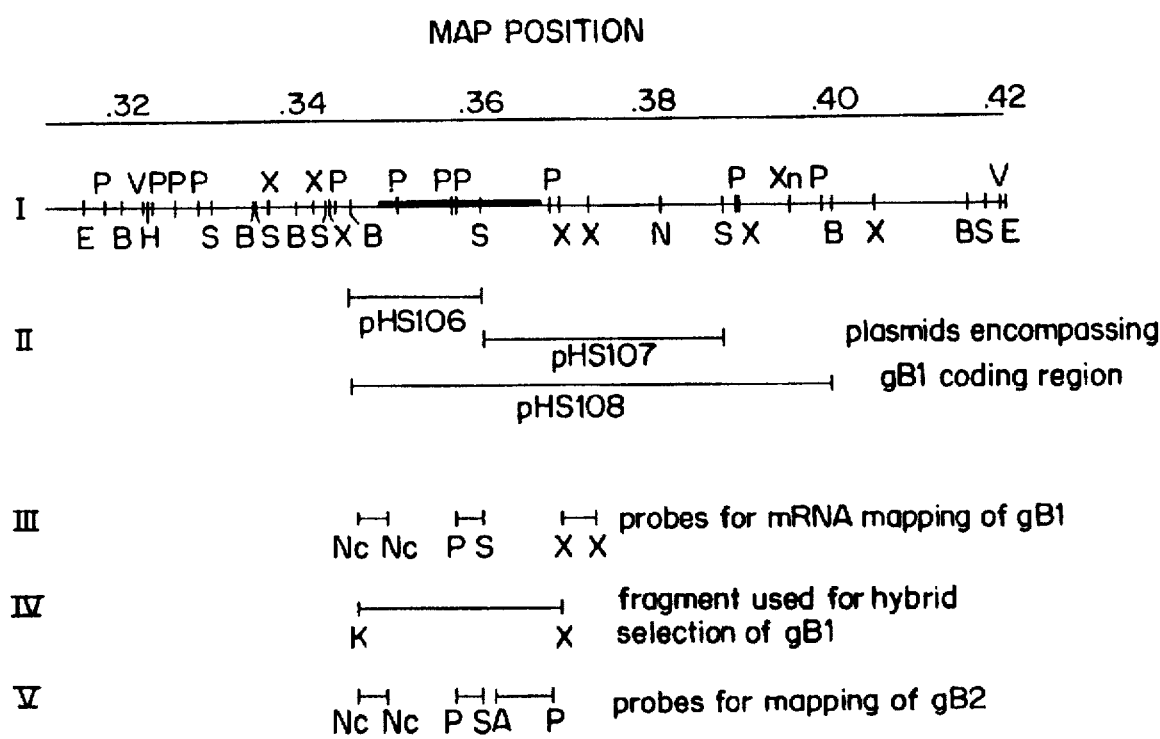
FIG. 2 is a restriction map of HSV-1 indicating coding regions for gB1.

In order to obtain the polynucleotide sequence encoding for gB1-Patton, the location of the gB1 coding sequences on the EcoRI restriction fragment F was mapped (see FIG. 1). Three subfragments of the F fragment were isolated and subcloned into pBR322 (FIG. 2). DNA fragments from these subclones were then used to probe Northern blots of Poly $A^+$ mRNA isolated from HSV-1 infected cells. Fragments which hybridized to mRNA of the size expected for gB were presumed to lie within the gB coding region. The direction of transcription of gB was also elicited by determining which strand of the DNA probes hybridized with the mRNA. To verify the identity of the gB sequence. DNA fragments were used to hybrid-select HSV-1 mRNA, which was then translated in vitro and the resulting proteins analyzed for gB using a gB-specific antibody.

The gB1 coding fragment may now be manipulated in a variety of ways, including restriction mapping and sequencing, so as to establish the restriction sites and the open reading frame regions for expression. The DNA sequence may then be restricted to provide for a sequence encoding the entire gB precursor or fragments thereof. These sequences may then be inserted into an appropriate expression vector having appropriately positioned transcriptional and, as appropriate, translation signals. As previously indicated, this can be achieved by filling in overhangs and providing for blunt-end ligation, by employing adapters, or the like.

Of particular interest is to introduce the gene in tandem with a gene capable of amplification. Convenient genes include the dihydrofolate reductase (dhfr) gene, which can be amplified by employing methotrexate, where the dhfr gene and flanking regions are reiterated, and metallothioneins which can be amplified with heavy metals, e.g., copper or the like. The expression product construct can be introduced into an appropriate host by any convenient means, including transformation, transfection, calcium phosphate precipitation, etc. The host cells may then be stressed with the appropriate biocide at levels which select for amplification of the particular gene. The cells may then be cultured and grown to provide efficient production of the desired polypeptide.

Following the procedure described above, the polynucleotide sequence coding for gB2 from a HSV-2 strain 333, both precursor and mature, may be isolated, cloned, and manipulated to provide a construct which may result in expression in one or more hosts. However, in view of the availability of fragments coding for gB1-Patton, these fragments may be used as probes for either localization of gB2 encoding DNA segments to specific HSV-2 restriction fragments or clone(s) or for isolation of gB2 mRNA from infected host cells. Conveniently, a plurality of probes may be employed coding for different regions of the gB1 gene. One selects for either positive DNA fragment(s) or abundant mRNA having approximately the right size which hybridizes to the probe(s). The mRNA may then be reverse transcribed to provide cDNA and/or may be used for hybridization to fragments of the HSV-2 genome to confirm their gB2 encoding function. Where necessary, more than one cloned fragment comprising portions of the gB2 structural gene may be manipulated and joined to provide the entire coding region and flanking region(s), as appropriate. The coding region may then be introduced into an expression vector.

gB may be used as a component of vaccines, particularly for humans. gB1 and gB2 may be used together or separately. They may be used neat, but will normally be used in conjunction with a physiologically acceptable medium, generally water, saline, phosphate-buffered saline, sugar, etc., and may be employed with a physiologically acceptable adjuvant, e.g., aluminum hydroxide, muramyl dipeptide derivatives, and the like. The vaccine may be delivered in liposomes and/or in conjunction with immunomodulators such as interleukin 2. The vaccines may be administered by any convenient route, e.g., intravenously, intraarterially, subcutaneously, intradermally, intramuscularly, or intraperitoneally. They may also be administered prior to and subsequent to an initial infection with HSV. It may be advantageous to administer split doses of vaccines which may be administered by the same or different routes. The amount employed per dose may be about 10 μg to 1 mg, if liquid, in a volume of about 0.25 to 1 ml, and may be administered repeatedly at daily to weekly intervals, usually not more than daily to two to ten times.

It is evident from the above that the entire oligonucleotide sequence or fragments thereof having functional significance may also be employed in a variety of other ways. The amino acid sequence or fragments encoded therein can be used by themselves or in combination with various labels in immunoassays, bioassays or the like, for the detection of HSV or antibodies to HSV, etc. Labels include radionuclides, enzymes, fluorescers, chemiluminescers, enzyme substrates or cofactors, enzyme inhibitors, particles, dyes, etc. These conjugates may be used in any convenient assay, such as enzyme immunoassays, e.g., ELISA, homogeneous enzyme immunoassays, fluorescence immunoassays, and the like. See, for example. U.S. Pat. Nos. 3,766,162; 3,791,932; 3,817,837; 3,996,345 and 4,233,402.

Experimental
1. Materials and Methods

The HSV-1 strain Patton and HSV-2 strain 333 viable stocks are available from Dr. Richard Hyman, Hershey Medical Center, Hershey, Pa. These viruses can be propagated in Vero cells available from Dr. Evelyn Linnette, Viro Labs, Emeryville, Calif., or from the American Type Tissue Culture Laboratory, the propagation being performed in accordance with standard procedures. A library of HSV-1 Patton EcoRI DNA fragments Kudler et al, *Virology* (1983) 124:86–99) cloned in the EcoRI site of the plasmid pACYC184 (Chang and Cohen, *J. Bacteriology* (1978) 134:1141) can be obtained from Dr. Hyman or be independently prepared in accordance with conventional techniques. Two HSV-2 333 clones can also be obtained from Dr. Hyman, namely the HindIII fragments H and L inserted into the HindIII site of pBR322 (Sutcliffe, *Nucleic Acids Research* (1978) 5:2721).

The dhfr deficient CHO cell line was obtained from Dr. Y. W. Kan (University of California at San Francisco). This cell line was originally described by Urlaub and Chasin, *Proc. Natl. Acad. Sci. USA* (1980) 77:4216–4220. For nonselective conditions, these cells were grown in Ham's-F-12 medium (available from Gibco. cat. no. 176) supplemented with 10% fetal calf serum. 100 U/ml penicillin, 100 μg/ml streptomycin and 150 μg/ml L-proline. Selective media was DME supplemented with 10% dialyzed fetal calf serum plus penicillin, streptomycin and 150 μg/ml L-proline. For methotrexate (MTX) selection, concentrated MTX stocks were prepared from MTX obtained from Lederle and added to the above DME selective media immediately before use.

1.1 Cloning

All DNA manipulations were done according to standard prozedures. See. Maniatis et al., *Molecular Cloning*, CSH (1982). Restriction enzymes. T4DNA ligase, *E. coli*. DNA polymerase I Klenow fragment, and other biological reagents were purchased from commercial suppliers and used according to the manufacturer's directions. Double-strand DNA fragments were separated on 1% agarose gels and isolated by electroelution.

1.2 Isolation of RNA, Northern blot analysis and hybrid-selected translation

Total RNA was prepared from HSV-1 or HSV-2 infected Vero cells at 6 hrs after infection with multiplicity of 10 pfu per cell. Cell monolayers were washed, incubated with extraction buffer and processed as described (Pachl et al., *Cell* (1983) 33:335–344). Poly A$^+$ RNA was prepared by passing 2 mg total RNA over a 3 ml column of oligo dT cellulose (obtained from Collaborative Research) in 500 mM NaCl, 10 mM Tris HCl pH 7.5, 1 mM EDTA, 0.1% SDS, then washing the column with 100 mM NaCl, 10 mM Tris HCl pH 7.5, 1 mM EDTA, 0.1% SDS and then eluting the poly A$^+$ fraction with 10 mM Tris HCl pH 7.5, 1 mM EDTA, 0.1% SDS.

For Northern blot analysis, poly A$^+$ RNA was denatured with glyoxal (McMaster et al., *Proc. Natl. Acad. Sci. USA* (1977) 74:4835–4838), fractionated by electrophoresis on 1% agarose gels, transferred to nitrocellulose paper (Thomas, ibid. (1980) 77:5201–5205) and hybridized with $^{32}$P-labeled probes.

The details of the methods used for hybrid-selected translations have been described previously (Pachl et al., *Cell* (1983) 33:335–344). DNA filters were prepared using 3 μg of a 3.5 kb Xho-Kpn fragment encoding gB or 2 μg of a 3.0 kb SstI-SstI fragment encoding HSV-1 glycoprotein gD. The filters were incubated with 40 μg of poly A$^+$ RNA from HSV-1 infected cells. Bound RNA was eluted and translated in a reticulocyte cell-free system (Pachl et al., *J. Virol.* (1983) 45:133–139). Translation products were analyzed on 12.5% sodium dodecyl sulfate (SDS) polyacrylamide gels (Laemmli, *Nature* (1970) 227:680).

1.3 DNA transfections

Transformation of COS 7 cells (Gluzman, *Cell* (1981) 23:175–182) or dhfr deficient CHO cells (Urlaub and Chasin, (1980) supra) was carried out using the procedure of van der Eb and Graham (*Methods in Enz.* (1980) 65:826–839), as modified by Parker and Stark (*J. of Virol.* (1979) 31:360–369), except that carrier DNA was omitted. A calcium phosphate precipitate of plasmid DNA was prepared by mixing an equal volume of plasmid DNA, in 250 mM CaCl$_2$, with an equal volume of 2× concentrated HEPES-buffered saline (2×HBS) added dropwise (1×HBS is 0.14M NaCl, 5 mM KCl, 0.7 mM Na$_2$HPO$_4$, 2.8 mM glucose, 10 mM HEPES pH 7.0). After about 20 min incubation at room temperature. 1 ml of the calcium phosphate-DNA suspension (containing 15 μg DNA) was added to the media of cells. grown to 50% confluency on 10 cm plates. After 6–8 hrs the DNA containing media was removed and the cells were incubated with 15% glycerol-1×HBS for 4 min. The cells were then grown in nonselective media (F12) for two days, after which the cells were split, i.e., subcultured, into selective media. Colonies of dhfr positive cells appeared after 10 days and were isolated after 14 days by removing the cells of a colony from a dish with a Pasteur pipette. The isolated cells were transferred to multiwell dishes for propagation.

1.4 In vivo labeling of cells and immunoprecipitation

To label with $^{35}$S-methionine, cells were grown to confluency in 3.5 cm dishes, washed once with PBS (0.14M NaCl, 2.7 mM KCl, 15.3 mM Na$_2$HPO$_4$) and then 0.5 ml of labeling media, DME (Dulbecco's Modified Eagle medium from Gibco, cat. no. 188G) without methionine plus 1% dialyzed fetal calf serum and 400 μCi/ml $^{35}$S-methionine (>1000 Ci/mmole) was added per dish. The cells were incubated for appropriate times at 37° C. At the end of the labeling period, the media was removed and the monolayer washed once with PBS. For a "cold" methionine chase, the labeling media was replaced with DME containing 2.5 mM methionine. For immune precipitation, cells were lysed in 0.1 ml of lysis buffer: 20 mM Tris-HCl pH 8, 100 mM NaCl, 1M EDTA, 0.5% Nonidet P40, 0.5% sodium deoxycholate, bovine serum albumin, 0.1% SDS, 1.0 mM phenylmethylsulfonyl fluoride, 10 mM benzamidine, 1% aprotenin obtained from Sigma Chemical Company. The cell lysate was scraped into tubes, briefly vortexed, and then held at 4° C. for 5–10 min. Cell debris was removed by centrifugation and the clarified lysate stored at –70° C.

For immunoprecipitations, cell lysates, 0.1 ml, were precleared by incubation with normal serum for 30 min at 4° C., then 50 µl of a 20% solution of protein A Sepharose (PAS) (in lysis buffer) was added and incubation continued for 30 min at 4° C. with gentle rocking. The PAS was removed by centrifugation for 1 min at 14,000×g and 5 µl of HSV-1 polyclonal antibody (obtained from DAKO) or a gB-specific monoclonal antibody F3AB (obtained from Dr. John Oakes, University of South Alabama) was added. When the F3AB antibody was used, 0.1% SDS was omitted from the lysis buffer. After min at 4° C., 75 µl of PAS was added and incubated as above. PAS-immune complexes were collected by centrifugation, washed 3× with lysis buffer lacking BSA and protease inhibitors and once with 0.12M Tris HCl pH 7.0. Immune precipitated proteins were released from PAS by boiling in SDS sample buffer, followed by analysis on 12% polyacrylamide gels. For immune precipitation of labeled proteins from cell media, the media was first clarified by centrifugation and then 1/10 volume of lox lysis buffer was added and proteins were precipitated as described above.

1.5 Immunofluorescence

To analyze expression of gB in COS cells or CHO clones, cells, grown in slide wells, were washed 3× with PBS, fixed with 100% methanol at –20° C. for 10 min followed by 3 more PBS washes and one wash with PBS plus 5% goat serum (GS). The fixed cells were then incubated with the primary antibody (HSV-1 or HSV-2 polyclonal diluted 1/100 in PBS-5% GS) for 30 min at 37° C. The cells were then washed 3× in PBS-5% GS and then incubated at 37° C. for 30 min with the second antibody. FITC-conjugated goat anti-rabbit IgG (Cappel), diluted 1/10 in PBS-5% GS. After 4 washes in PBS-5% GS, the slides were mounted with coverslips using 50% glycerol—100 mM Tris HCl, pH 8 and observed in a Leitz microscope equipped with epifluorescent optics. Live cell immunofluorescence was carried out as described above except that the cells were initially washed once in PBS-5% GS directly followed by incubation with the first antibody. Before mounting with coverslips, the live cells were fixed with 5% formaldehyde in PBS. The fluorescein stained cells were photographed using a Kodak Ektachrome film (ASA 400).

1.6 ELISA Assay

The concentration of gB protein in CHO cell conditioned medium was measured by an indirect enzyme-linked immunoadsorbent assay (ELISA) using a preparation of purified recombinant gB as a standard. Aliquots of 50 µl of F3AB, a gB-specific monoclonal antibody (Rector et al. *Infect. and Immun.* (1982) 38:168–174), diluted 1:1000 in PBS were adsorbed to the wells of a 96-well polyvinyl chloride plate (Dynatech Laboratories, Inc.) by incubation for 1 hr at room temperature. Excess antibody was removed by 3 washes with PBS-5% GS. 50 µl aliquots of media samples or the gB protein standard diluted in PBS+1% GS were added to the wells and incubated for 1 hr at room temperature. The plates were then washed 3 times with PBS+1% GS (goat serum) and followed by a third 1 hr incubation with 50 µl of rabbit anti-HSV-1 polyclonal antibody (obtained from DAKO) diluted 1:100 in the same buffer. Excess secondary antibody was removed by 3 washes with PBS+1% GS. Finally, 50 µl of goat anti-rabbit horseradish peroxidase-conjugated antibody (Boehringer Mannheim) diluted 1:500 in PBS+1% GS was added to each well for a 1 hr incubation. The wells were then washed once with PBS+1% GS, followed by 8 washes with PBS and then developed with 50 µl of 2.2µ-azido-di-[3-ethyl benzthioazoline sulfonate] (Boehringer Mannheim) at a concentration of 1 mg/ml in 0.1M citric acid, pH 4.0, 0.003% $H_2O_2$. The color reaction was stopped after 5 minutes by the addition of 50 µl of 10% sodium dodecyl sulfate (SDS) and the absorbance was read at 414 nm in a microtiter plate reader.

1.7 Yeast transformation

Yeast were transformed (Hinnen et al., *Proc. Natl. Acad. Sci.* (1978) 75:1929) and grown using a variety of media including selective medium (yeast nitrogen base without leucine): YEPD medium, containing 1% (w/v) yeast extract, 2% (w/v) peptone and 2% (w/v) glucose, and others as appropriate and/or detailed below. Plating medium contained 2% (w/v) agar and for transformation 3% top agar.

2. Glycoprotein B.1

2.1 Isolation, cloning and characterization of the gB1 gene

To isolate the gene for the glycoprotein gB1. DNA fragments spanning map coordinates 0.345 to 0.40 within the EcoRI F restriction fragment of the HSV-1 strain Patton (Skare and Summers, *Virology* (1977) 76:581–595) were subcloned in the plasmid pBR322. These fragments were prepared from the appropriate restriction digests of the EcoRI region in the plasmid pACYC184, separated by electrophoresis on a 1% agarose gel in TAE buffer (0.04M Tris-acetate, 0.002M EDTA) and electroeluted as noted above. The isolated fragments were ligated into pBR322 which had also been previously cut with the appropriate restriction enzyme and treated with alkaline phosphatase. A restriction map for the entire HSV-1 genome is shown in FIG. 1, and a more detailed map of the region which was subcloned is shown in FIG. 2. Referring to FIG. 1, the conventional map is shown in the first two lines (Roizman, 1979). The dotted line indicates the L-S junction. The restriction enzyme cleavage map for EcoRI for the prototype isomer arrangement is shown in the third line (Skare and Summers, 1977; Roizinan, 1979) with the EcoRI fragment F denoted by the cross-hatched box. For HSV-2, the HindIII restriction map is shown in line 4 (Roizman, 1979) with the HindIII fragment H cross-hatched. One map unit corresponds to approximately 98.9 megadaltons or 148.9 kbp of DNA for HSV-1 and 105.6 megadaltons or 160.5 kbp of DNA for HSV-2.

Referring to FIG. 2, the restriction enzyme sites shown in the detailed map line (I) are E, EcoRI; B, BamHl: S, SalI; P, PstI, X, XhoI from DeLucca et al., 1983; N, NdeI; Xn, XmnI; V, EcoRV. The BstEII site mapped by DeLucca et al. at 0.355 is missing in this strain and there is a new PstI site at 0.357. Line II shows three plasmid subclones which encompass the gB1 coding region. They are pHS106, which extends from the BamHI site at 0.345 to the SalI site at 0.360; pHS107 which extends from the SalI site at 0.36 to the SalI site at 0.388: and pHS108 which is a BamHI fragment extending from 0.345 to 0.40 map units. Line III indicates three probes used for mRNA mapping of gB1; line IV indicates the fragment used for hybrid selection; and line V shows those probes used to locate the gB2 gene (see below). The additional restriction sites used to generate these fragments are Nc, NcoI; K, KpnI; and A, AluI.

To locate the gB1 coding region within the EcoRI F fragment. Northern blots of poly $A^+$ mRNA isolated from HSV-1 infected Vero cells were probed with the DNA fragments indicated on the detailed map isolated from plasmids pHS106 and pHS107. When HSV-1 mRNA was probed with a 0.56 kb PstI-SalI fragment isolated from pHS106, a 3 kb mRNA was the major species detected. When the same blot was probed with a 0.49 kb NcoI fragment, which maps about 1 kb upstream from the PstI-SalI fragment, hybridization to a 3 kb mRNA, the presumptive gB1 mRNA, was also detected. This suggests that the gB1 coding sequences extend at least 1 kb to the left of the PstI-SalI fragment. The 3 kb mRNA does not extend beyond the first XhoI site downstream from the PstI-SalI fragment, since the 0.5 kb XhoI-XhoI fragment does not hybridize to this mRNA. The direction of transcription of the gB1 transcription unit is right to left (3'←5') as evidenced by hybridization of only the 5'→3' oriented strands of the PstI-SalI and NcoI-NcoI fragments (cloned in M13) to the 3 kb gB1 mRNA.

Hybrid selected translation was performed by hybridizing HSV-1 poly A+ mRNA with a 3.2 kb KpnI-XhoI fragment, which encompasses the region indicated as encoding gB1. When the bound MRNA was eluted and translated in vitro, a 100 kd protein, similar in size to gB1 from HSV-1 infected Vero cells, was detected. Confirmation of the identity of the 100 kd protein was achieved by immunoprecipitation with a gB1-specific monoclonal antibody. Several other proteins were also detected by hybrid selection using the KpnI-XhoI fragment, probably the result of non-specific hybridization of mRNAs due to the high G+C content of the DNA. A similar pattern of proteins was seen when the same RNA was selected with a 3.0 kb SstI-SstI DNA fragment encoding HSV-1 glycoprotein gD, except that the 100 kd gB protein was not detected. This result indicates that gB is specific to the XhoI-KpnI fragment.

Figure 3:
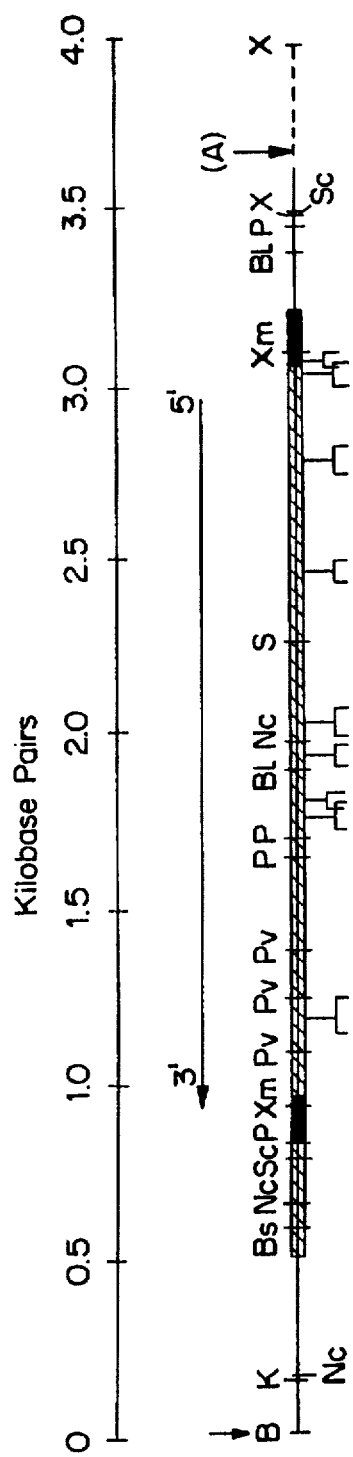
FIG. 3 is a restriction map of the gB1 coding region.

FIG. 3 is a restriction map of a 3.95 kb DNA fragment, which extends from a BamHI restriction site at 0.345 to an XhoI site at 0.373 map units. The open reading frame for gB1 is indicated by the box and the direction of transcription is from right to left as shown. The actual coding region covers map units 0.348 to 0.367. The DNA sequence from the BamHI site to a non-unique AluI site at nucleotide number 3640 is shown with the AluI site indicated by the (A). The restriction sites shown include B, BamHI; Bl, BalI; Bs, BstEII; K, KpnI; Nc, NcoI; P, PstI; Pv, PvuII; S, SalI; Sc, SacI, X, XhoI; Xm, Xma3. Restriction sites are not shown for the right-hand end from the AluI site to the terminal XhoI site. Potential glycosylation sites and, hydrophobic anchor and signal regions (solid box) in the product gB1 protein are noted.

The DNA sequence was determined from the BamHI site to a non-unique AluI site at nucleotide residue number 3640 using the M13 dideoxynucleotide synthesis method of Sanger. Both DNA strands across the coding region were sequenced. The entire DNA sequence was compiled from overlapping restriction fragments such that the sequence was read across all restriction fragment joints. FIG. 4 shows the DNA sequence for gB1 (line 3); the predicted amino acid sequence for gB1 is shown below the DNA sequence (line 4).

It should be noted that the amino acid sequence and DNA sequence for gB1 presented in FIG. 4 differs from that originally presented in Table 1 of the parent application, Ser. No. 597,784, filed Apr. 6, 1984, the disclosure of which is hereby incorporated by reference. The DNA sequence in said Table 1 contains errors which may be corrected by the insertion or deletion of nucleotides as follows (all numbers refer to the positions of the nucleotides in Table 1):

(1) insert G between positions #227–#228, in the 5'-untranslated region;
(2) delete G at position #607;
(3) add C between positions #737–#738;
(4) delete C at position #1155;
(5) add G between positions #1235–1236;
(6) add CG between positions #1690–1691;
(7) add G between positions #1718–1719;
(8) substitute G for A at position # 2037; and
(9) delete G at position #3304 in the 3'-untranslated region.

The amino acid sequence in Table 1 was deduced from the incorrect DNA sequence presented therein, and is therefore incorrect. FIG. 4 presents the amino acid sequence based upon the corrected DNA sequence; the amino acid sequence in FIG. 4 has been confirmed by amino acid sequencing of the N-terminal region of gB1. This change in the deduced amino acid sequence also results in correction concerning the deduced position of the hydrophobic and hydrophilic regions, and the glycosylation sites in the gB1 molecule. The deductions based upon the corrected sequence are presented below.

Primer extension, using a 22 bp oligonucleotide (residues 473–494) indicated that the 5'-end of gB1 mRNA was located at residue 188. The CAT and TATA transcriptional regulatory signals are presumptively at residues 55–62 and 125–131. Starting at the ATG at residues 438–440, there is an open reading frame of 2712 nucleotides which terminates at a TGA stop codon. Two presumptive polyadenylation signals are located in a 3'-non-coding region at residues 3166–3173 and 3409–3416.

The observed amino acid sequence is characteristic of a membrane protein. There is a very hydrophobic region near the carboxy terminus stretching from amino acid residue number 726 to 795, a 69-amino acid sequence which may span the membrane. At the N-terminus the first 30 amino acids are primarily hydrophobic. This hydrophobic amino acid domain precedes a region with a high concentration of charged or hydrophilic amino acids. The hydrophobic sequence at the N-terminus may serve as a secretory leader or signal sequence followed by processing signals for cleavage and removal of the secretory leader. The hydrophobic region near the C-terminus can serve as a transmembrane integration sequence for binding the protein to the cell membrane.

The sequence data is also suggestive that there are nine possible N-linked glycosylation sites as defined by the sequence asn-X-thr/ser (see also FIG. 3) within the hydrophilic, external domain. If the first 30 amino acids are removed by processing and each of the potential N-linked glycosylation sites are utilized with the addition of an average 2 kd of carbohydrate per site, the molecular weight of the mature protein would be approximately 123 Kd.

2.2 Expression of gB1 in mammalian cells

Employing the above DNA sequence or fragment thereof, expression was achieved as follows. The vector employed is a mammalian expression vector, referred to as pSV1/dhfr. This 5.63 kb plasmid contains 2.8 kb of *E. coli* plasmid pBR328 sequences, including the ampicillin-resistance β-lactamase gene and the origin of replication. The vector also contains a selectable mammalian cell marker, the mouse dihydrofolate reductase cDNA gene (dhfr) (Nunberg et al., *Cell* (1980) 19:355) linked to the SV40 early promoter, which directs the transcription of dhfr. Additional SV40 sequences, including t antigen splice donor and splice acceptor sites and the polyadenylation sites for early transcripts, are included downstream from the dhfr gene within a 1.65 kb BglII-EcoRI fragment.

Figure 5:
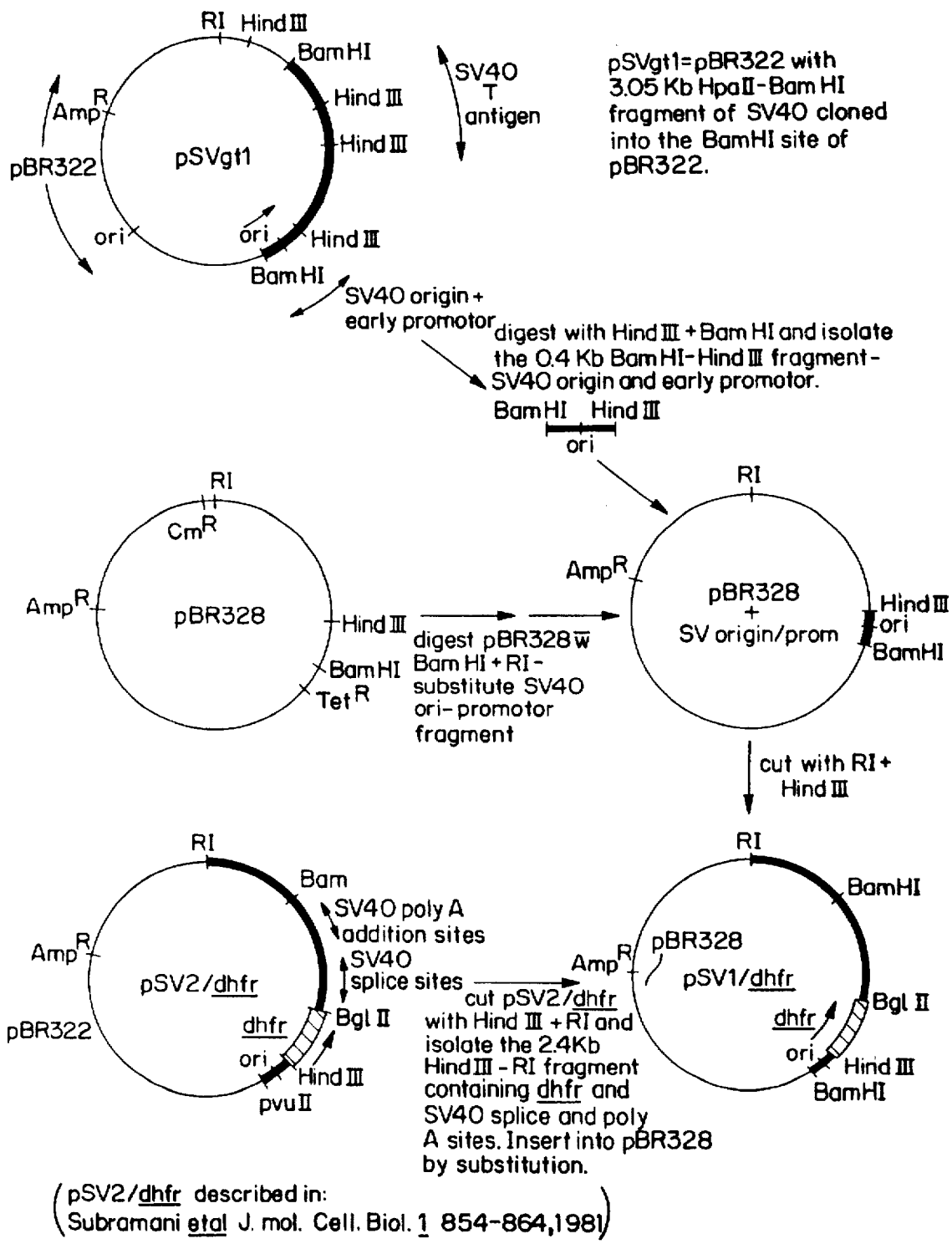
FIG. 5 is a flow diagram of the construction of pSV1/dbfr, a mammalian expression vector.

The plasmid pSV1/dhfr was constructed by first isolating the 0.4 kb BamHI-HindIII fragment encoding the SV40 origin and early promoter from plasmid pSVgt1. This SV40 fragment was then inserted into plasmid pBR328 by substituting this fragment for the small HindIII-BamHI fragment of pBR328. The dhfr cDNA gene and the SV40 splice sites and poly A sites of pSV1/dhfr were derived from plasmid pSV2/dhfr (Mulligan and Berg, *Mol. Cell Biol.* (1981) 1:854–864). The 2.4 kb HindIII-RI fragment encoding the dhfr-SV40 sequences was excised from pSV2/dhfr and inserted into the above pBR328 plasmid by substitution for the small HindIII-RI fragment of pBR328. The details of these constructions are given in FIG. 5.

Figure 6:
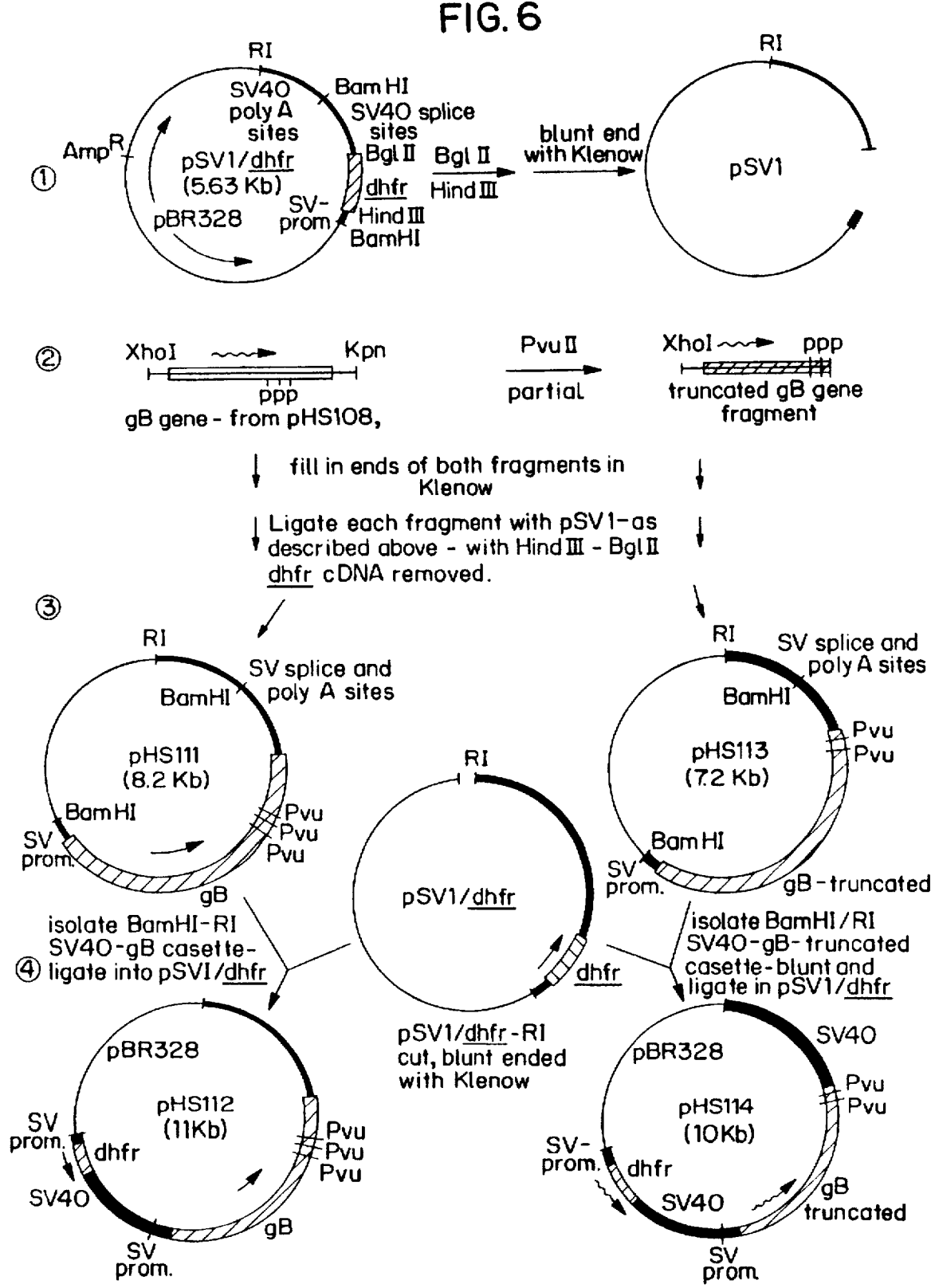
FIG. 6 is a flow diagram of the construction of plasmids pHS112 and pHS114, mammalian expression vectors for gB1.

To obtain expression of gB1, two pSV1/dhfr-gB plasmids, pHS112 and pHS114 were constructed (FIG. 6). The plasmid pSV1/dhfr was restricted with BglI and HindIII excising the dhfr cDNA fragment. The resulting fragments were then blunt-ended by filling in the overhangs with the Klenow fragment of DNA polymerase I. A XhoI-KpnI HSV-1 fragment containing the gB gene was isolated from pH108. A portion was taken and partially digested with PvuII to generate a DNA sequence lacking the 3'-anchor region. The resulting truncated gB1 gene lacks 580 bp from the 3'-end of the gene. Both fragments were then blunt-ended with the Klenow fragment of pol I.

Each gB blunt-ended fragment was ligated into the BglII-HindIII restricted pSV1/dhfr vector to provide two sets each of constructs, with the gB1 gene in opposite orientations. The orientations having the Xho generated terminus proximal to the SV-40 promoter, with the direction of transcription being from the SV-40 promoter to the SV-40 splice sites selected and designated pHS111 and pHS113 for the complete and truncated gB1 genes, respectively. The two plasmids were then completely digested with EcoRI and partially digested with BamHI to provide a cassette which includes the SV-40 promoter, the gB gene and the SV-40 splice and polyadenylation sites. These fragments were blunt-ended and ligated into EcoRI digested pSV1/dhfr vectors, so as to have the gB1 gene downstream from the dhfr gene and in the same orientation. The complete gB1 gene and truncated gB1 plasmid constructs are designated pHS112 and pHS114, respectively.

The plasmids were then transfected into CHO cells deficient in dhfr using the calcium phosphate precipitation method as described in Materials and Methods. Transfected cells were selected by employing a selective medium lacking thymidine, purines and glycine. Cells were isolated by removal with a Pasteur pipette and propagated in multiwell plates. A number of clones were isolated which were shown to produce gB by immunofluorescence and radioimmunoprecipitation employing an HSV-1 polyclonal antibody or a monoclonal antibody specific for gB. Three cell clones, pHS112-1, pHS112-9 and pHS112-23, were isolated which synthesize an intracellular form of the complete gB protein. The gB made in these cells appears to be glycosylated, since higher molecular weight forms can be detected after a one hour pulse, followed by a 5 hr chase, as compared to non-chased cells and about 10% of the gB is secreted into the media. Five cell clones (pHS114-5, pHS114-6, pHS114-7, pHS114-11 and pHS114-12) expressing the truncated gB were also analyzed and shown to also secrete some gB into the media. One of these cell lines, pHS114-7, was chosen for further amplification with MTX. Clones were initially selected at 0.01, 0.05, 0.10 and 0.3 μM MTX. Three clones synthesizing high levels of gB, as detected by immunofluorescence, were isolated from the 0.3 μM MTX selections. By radioimmune precipitation, these clones, pHS114-0.3 μM-6, 23 and 25, synthesize 2–3 times more gB during a 1 hr labeling with $^{35}$S-methionine than the unamplified clone, pHS114-7. Pulse chase experiments indicate that at least 8% of the gB synthesized in these clones during a 1 hr pulse is secreted extracellularly by 5 hr.

2.3 Expression of gB1 in yeast

Yeast expression was developed as follows. A cassette was prepared employing the glyceraldehyde-3-phosphate-dehydrogenase (GAPDH) promoter region and terminator region. A yeast gene library was prepared by inserting fragments obtained after partial digestion of total yeast DNA with restriction endonuclease Sau3A in lambda-phage Charon 28 (Blattner et al., *Science* (1977) 196:161–169). The phage library was screened with DNA complementary to the yeast GAPDH mRNA and the yeast GAPDH gene from one of these clones was subcloned as a 3.5 kb BamHI fragment in the BamHI site of pBR322 (pGAP-2). The GAPDH promoting-active fragments were isolated from these clones. A HhaI-HindIII fragment of about 350 bp containing the 3' portion of the promoter was obtained by: a) digestion of pGAP-2 with HinfI to generate an approximately 500 bp segment which includes the 3' part of the promoter and a region encoding the N-terminal amino acids of GAPDH; b) resection with Bal31 to yield a 400 bp fragment lacking the GAPDH coding region (3'-terminus 1 base upstream from the ATG initiator codon): c) addition of HindIII linkers; and d) leavagr with HhaI. A HindIII-Hha fragment of about 700 bp containing the 5' portion of the promoter was ligated to the 350 pb HhaI-HindIII fragment and treated with HindIII. The resulting 1061 bp HindIII fragment was isolated by gel electrophoresis and cloned in pBR322 (pGAP-347). The GAPDH promoter fragment in pGAP-347 was isolated by cleavage with BamHI (within the 5' pBR322 flanking region) and partially with HindIII (at the 3' end of the promoter fragment) to provide a 1407 bp fragment containing a 1061 bp region of the GAPDH promoter region and 346 bp of pBR322. This procedure utilized digestion of 50 μg of the pGAP-347 with 10 units each of BamHI and HindIII with the resulting fragment purified by preparative gel electrophoresis in 1% agarose.

A synthetic HindIII-XhoII adapter molecule containing the codon for the initiator met and a NcoI site for analysis was synthesized and had the following sequence:

AGCTTCCATGGA AGGTACCTCTAG.

A third fragment was a XhoII-SacII fragment of 1187 bp containing the gB1 coding region.

A fourth fragment containing the GAPDH terminator fragment (approximately 900 bp) was isolated by SalI-BamHI digestion of a cloned fragment of the GAPDH gene with its 3' flanking region including the GAPDH termination region, so that a portion of the coding region is included with the termination region. The two fragments can be ligated together by means of a SacII-SalI adapter:

GGACAACTAG CGCCTGTTGATCAGCT.

These five fragments together with the cloning vector were ligated as follows: First, the XhoII-SacII fragment (2 picomoles) was ligated to 100 picomoles of each of the two adapters (HindIII-XhoII, SacII-SalI) using T4 DNA ligase. The product was isolated by preparative gel electrophoresis in 1% agarose, providing a HindIII-SalI fragment. The HindIII-SalI fragment (0.25 picomoles) was ligated in a single step to the 1,407 bp BamHI-HindIII GAPDH promoter fragment (0.1 picomoles), the 900 bp SalI-BamHI terminator (0.1 picomoles) and 0.02 picomoles of BamHI-digested, phosphatased pBR322 in the presence of T4 DNA ligase.

The above reaction product was used to transform *E. coli*. HB101. Plasmids containing the cassette clones in pBR322 were isolated and the correct nucleotide sequence confirmed by DNA sequencing. This plasmid was then digested with BamHI, and the BamHI cassette fragment containing the gB1 segment and GAPDH regulatory regions gel was isolated and was inserted into BamHI-digested, phosphatased pC1/1. Plasmid pC1/1 is a derivative of pJDB219 (Beggs, *Nature* (1978) 275:104) in which the region corresponding to bacterial plasmid pMB9 in pJDB219 is replaced by pBR322 in pC1/1. The pC1/1 plasmid containing the 1187 bp gB1 insert and GAPDH promoter and terminator regions was designated pHS127A. This plasmid was then used to transforn, the yeast strain *S. cerevisiae* AB103.1 (α, pep 4-3, leu 2-3, leu 2-112, ura 3-52, his 4-580). Transformants were initially grown in 1.0 ml of leu medium and then 50 ml of YEPD inoculated with 0.4 ml and grown further to an absorbance of 1–3 at 650 nm (12 hr). The yeast cells were pelleted by centrifugation at 2 krpm for 10 min at 4° C. and resuspended in 50 mM Tris-HCl, pH 8, 150M NaCl, 0.2% Triton X-100, 1 mM EDTA and freshly added 1.0 mM phenylmethylsulfonyl fluoride and 0.1 µg/ml pepstatin. The cells were repelleted and then resuspended in a volume equal to the packed cell volume in the same buffer. An equal volume of acid-washed glass beads (diameter 0.45–0.5 mm) was added and the yeast cells disrupted by vortexing at 4° C. for 10 min total, using 1 min intervals.

The tubes were centrifuged for 15 min at 14000×g at 4° C. and the supernatant isolated and analyzed on 10% SDS polyacrylamide gel and blotted onto nitrocellulose paper for Western analysis (Burnett, *Anal. Biochemistry* (1981) 112:195). A polyclonal antibody (DAKO) to HSV-1 was employed as the primary antibody. Expression of an HSV specific protein was observed at about 44 kd, the size expected for the gB fragment.

3. Glycoprotein B.2

3.1 Isolation, cloning and characterization of the gB2 gene

Figures 7A, 7B:
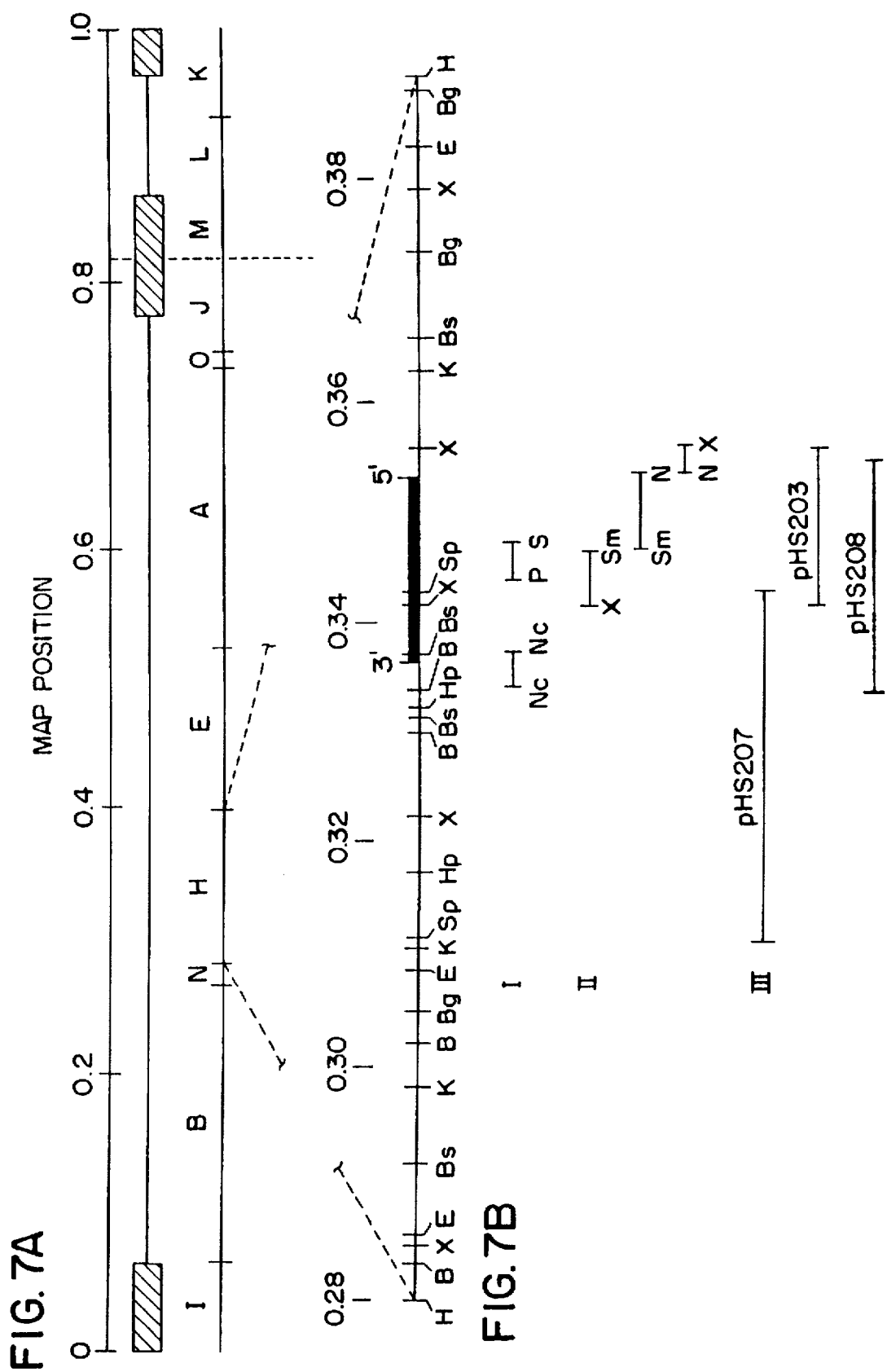
FIG. 7 is a physical map of HSV-2, indicating coding regions for gB2, and showing the origination of the oligonucleotides inserted into the cloning vectors.

The gene encoding glycoprotein B of HSV-2 had been shown to be colinear with the corresponding HSV-1 gB gene by analysis of HSV-1×HSV-2 intertypic recombinants and to lie approximately between prototypic map coordinates 0.30 and 0.42 (Ruyechan et al., *J. Virol.* (1979) 29:677–697). Thus, the HindIII H fragment of HSV-2 which spans map coordinates 0.28 to 0.40 (FIG. 7) includes the gB2 coding region. FIG. 7A shows a conventional prototype HSV-2 configuration in the first two lines. The restriction map for HindIII is shown in the third line. In addition to their colinear map location, serological and heteroduplex analyses indicate the close similarity of gB1 and gB2.

The gene for glycoprotein gB2 was located by hybridization with specific DNA probes generated from the gB1 coding region. As a first step, a restriction map was determined for the HindIII H fragment of HSV-2 strain 333 which spans map coordinates 0.28–0.39 as shown in FIG. 7B.

A random library of HSV-2 strain 333 sequences cloned into the lambda vector L-47.1 (Leonen and Brammar, *Gene* (1980) 10:249) (obtained from Dr. James Casey, Louisiana State University) was generated by a partial MboI digestion of the viral DNA and cloned into the BamHI site of the vector. The library was screened for plaque hybridization using a KpnI-NdeI fragment of gB1 as a probe. A positive lambda clone was picked and the lambda DNA prepared and digested with SphI (Maniatis et al., *Molecular Cloning*, Cold Spring Harbor Laboratory, 1982). A Southern blot analysis show that the gB2 information was contained within a 4.2 kb fragment. The SphI-digested lambda DNA was ligated to SphI-digested pBR322 and the mixture used to transform *E. coli* HB101. The appropriate transformant was selected by restriction analysis and confirmed by Southern blot analysis.

Three DNA pieces from the gB1 gene were used as probes to Southern blots of restriction digests of the HindIII H fragment, a 0.93 kb PstI-AluI piece from the 5'-end of the gene, a 0.54 kb PstI-SalI piece from the central region and a 0.9 kb NcoI-NcoI piece from the 3'-end. These fragments are shown in line V of FIG. 2. The hybridization pattern observed indicated that the gene spanned the two XhoI-XhoI fragments of 2.6 kb and 2.75 kb. (See FIG. 7, which shows a restriction map of the HindIII H fragment, in which gB2 is encoded. The restriction sites included are for B, BamHI; Bg, BglII; Bs, BstEII; E, EcoRI; H, HindIII; Hp, HpaI; K, KpnI; Sp, SphI; X, Xho I; Nc, NcoI; P, PstI; S. SalI, N, NruI, Sm, SmaI.) The gB2 gene was cloned in a pBR322 derivative as two overlapping fragments. The 5'-end is contained within pHS203, a 2.6 kb XhoI-XhoI clone, and the 3'-end within the adjacent 4.2 kb SphI-SphI fragment, pHS206, indicated on the above figure.

Figure 8:
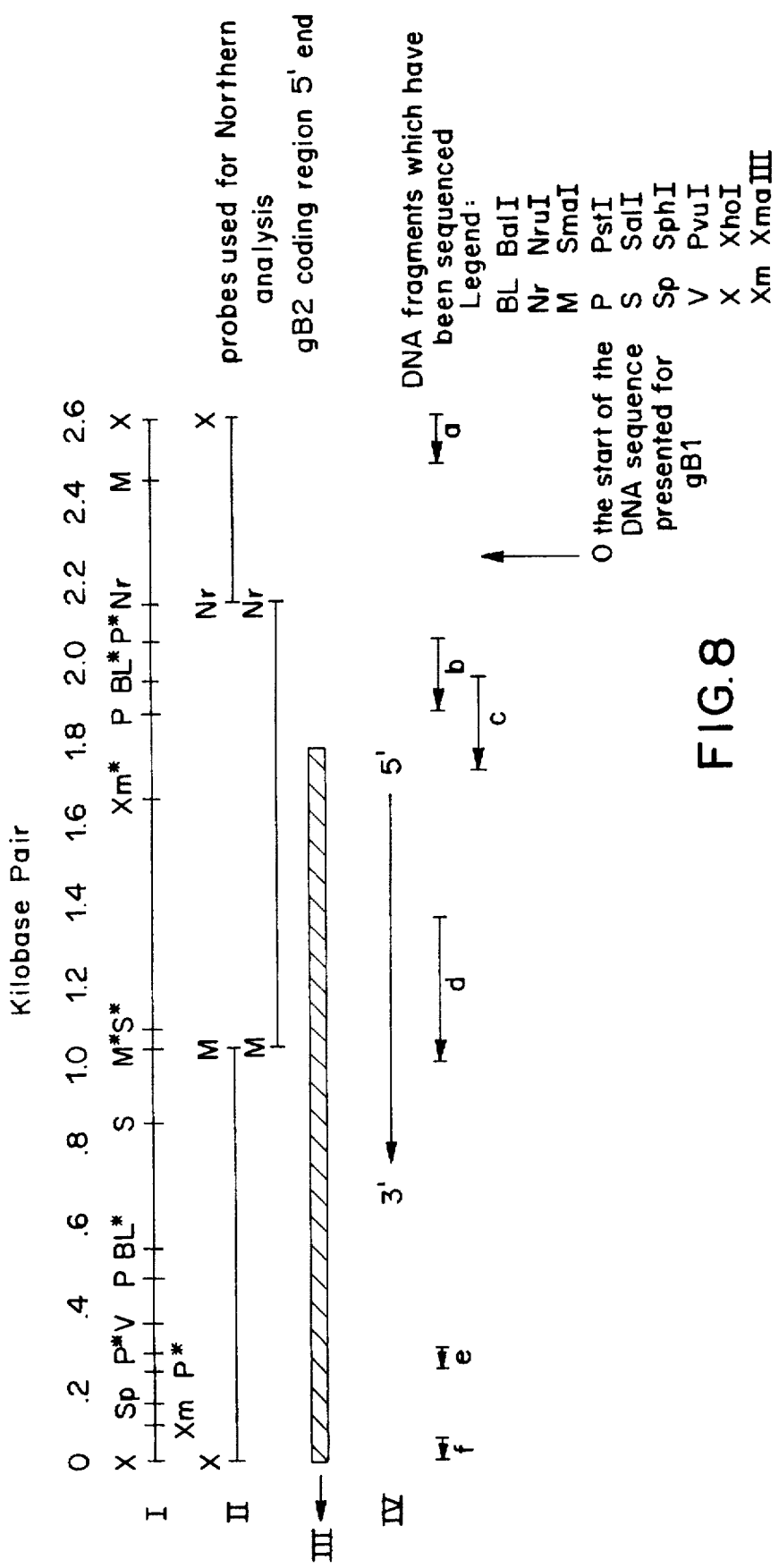
FIG. 8 shows a restriction map of the gB2 insert in pHS203.

A restriction map of the gB2 insert in the pHS203 XhoI subclone is shown in FIG. 8. The insert in pHS203 is a 2.6 kb XhoI-XhoI fragment which contains the 5'-end of the gene encoding gB2. Line I shows a restriction map which includes the restriction sites for B1, BalL; Nr, NruI; M, SmaI; P, PstI; S, SalI; Sp, SphI; V, PvuI; X, XhoI; Xm, XmaIII. Those restriction sites marked by an asterisk are conserved between the DNA sequences of gB1 and gB2. Line II shows three DNA fragments which were prepared by restriction digestion of pHS203 DNA and isolated by preparative gel electrophoresis and electroelution from a 1% agarose gel. These pieces were used to probe Northern blots of mRNA from HSV-2-infected Vero cells to map precisely the location of the gB2 gene. Line III indicates the direction of transcription from right to left. Line IV locates those DNA fragments of pHS203 which have been sequenced on the genetic map. The start of the DNA sequence, nucleotide 1, for gB1 is also noted by the arrow.

The exact location and the identity of the gB2 gene were verified by probing a Northern blot of poly $A^+$ mRNA isolated from HSV-2-infected Vero cells with the restriction fragments of pHS203, shown in FIG. 7B line II. Both an 0.89 kb XhoI-SmaI and a 1.29 kb SmaI-NruI fragment hybridized to an abundant 3.0 kb message, an appropriate size and representational frequency for gB2 based on analogy to the analysis of gB1 transcripts. However, the same message did not hybridize to the rightmost 0.47 kb NruI-XhoI fragment. As expected a similar hybridization pattern was observed when poly A RNA prepared from HSV-1 infected Vero cells was probed with these same fragments, although the signal intensity was diminished due to the inefficiency of cross-hybridization. Since this analysis indicated both the limit of the righthand end of the gB2 gene as well as its size, it was apparent that the gB2 coding sequences must extend an additional 1 kb to the left of those sequences contained within pHS203 into the overlapping pHS207 plasmid. Therefore, the gB2 gene was cloned as one continuous fragment of the 1.98 kb NruI-SphI fragment of pHS203 to the 1.48 kb SphI-BamHI fragment of pHS207 and insertion into NruI and BamHI-digested pBR322 to generate pHS208. The relationship of pHS203, pHS207, and pHS208 is shown in FIG. 7. It should be noted that both pHS206 and pHS207 contain the same 4.2 kb SphI-SphI fragments.

From a comparison of the HSV-1 and HSV-2 restriction maps, some of the restriction sites are conserved between the two species. To corroborate further the location of the gB2 gene and its homology with the gB1 gene, DNA sequence analysis of selected regions of the gB2 gene were determined.

The sequence of the fragments was presented in the above referenced application, Ser. No. 597,784, filed Apr. 6, 1984, and is shown as follows in FIG. 9. including a comparison of the sequence of the 5'-end of gB1 and gB2 for other than fragment DNA a. FIG. 9 presents a comparison of the homology between the DNA sequences b through f of HSV-2 gB2 and HSV-1 gB1. The top line of each comparison is the gB1 sequence and the number given is the nucleotide base pair of that same sequence. The bottom line is the corresponding gB2 fragment. Loop out regions or spaces have been inserted as required to display the maximum homology.

The HSV-2 fragment encoding gB was sequenced on both strands in its entirety. The complete nucleotide sequence for gB2 is shown in FIG. 4, line 2. The predicted amino acid sequence of gB2 is shown above the DNA sequence. For comparison, the DNA sequence and the amino acid sequence of gB1 from HSV-1 strain Patton is shown below. Spaces have been inserted into the sequence to permit maximal alignment of the two proteins. All numbers on FIG. 4 refer to the gB2 sequence. Characteristic TATA and CAT transcriptional regulatory sequences are most likely located 5' to the start of this sequence analysis analogous to the gB1 sequence. In the 3' non-coding region, a polyadenylation signal, AATAAAAA (Proudfoot and Brownlee, Nature (1976) 263:211) at residues 2744 to 2751 is the probable termination site of the gB2 mRNA.

The discrepancies between the partial sequences in FIG. 9 and the correct total nucleotide sequence for gB2 shown in FIG. 4 are due to technical errors in the interpretation of the DNA sequences of the gB2 fragments in FIG. 9. The sequences in FIG. 9 may be corrected by the following insertions and deletions in the shown nucleotide sequences (positions with a space are counted as a number).

Fragment b:

(1) change C to A at position #173;

(2) change T to A at position #174;

(3) change A to T at position #177; and (4) change G to T at position #178.

Fragment c:

(1) delete C at position #13;

(2) delete C at position #88;

(3) change C to A at position #95;

(4) change T to A at position #96;

(5) change G to T at position #100;

(6) change G to C at position #133;

(7) change C to G at position #134;

(8) change C to G at position #137;

(9) change G to C at position #138;

(10) add C at position #143;

(11) add G at position #146;

(12) delete C at position #212

(13) add G at position #219; and

(14) add G at position #221.

Fragment D:

(1) change A to T at position #19;

(2) change T to A at position #20;

(3) delete T at position #58;

(4) change G to T at position #60;

(5) Change C to G at position #110;

(6) delete C at position #152;

(7) delete C at position #170;

(8) add CG at positions #175–176;

(9) change C to G at position #193; and

(30) add CC between positions #319–#320.

Fragment f:

(1) add CC between positions #35–36.

There is a potential transmembrane anchor region of 54 amino acids from $Ala_{745}$ to $Leu_{798}$. Chou and Fasman analysis (Adv. Protein Chem. (1978) 47:45–148) indicates a mixed β-sheet and α-helix potential for the entire region. However, in order to avoid orientation of the membrane bilayer, it is likely that this region adopts an α-helical conformation (Engelman and Steitz, Cell (1981) 23:41–422). An α-helix of this length (8.1 nm) would be more than sufficient to span a biological membrane 3 nm in thickness 2 times, placing the C-terminal domain of the protein on the exterior of the cell. Alternatively, the transmembrane domain may traverse the membrane 3 times and include the amphipathic domain beginning at $Asp_{723}$ that contains 4 additional charged residues. In this analysis, tight-packing of the 3 α-helices allows interchain hydrogen bonding between the charged residues, all of which are predicted to lie on the same face of the helix. Thus, the charged residues would be thermodynamically allowed with the membrane, as they would not interact with the hydrophobic lipid environment. This model would localize the C-terminus of the protein within the cytoplasm. While it is not presently possible to distinguish between the possibilities that the gB anchor spans the membrane two or three times, it is an important consideration in terms of positioning the C-terminus on the extracellular or cytoplasmic side of the membrane.

The C-terminal region of gB2 extends from the end of the membrane anchor region at $Leu_{798}$ to the end of the protein at $Leu_{904}$ and contains a high density of charged residues. No potential N-linked glycosylation sites are present in this portion of the Type 2 protein.

The predicted gB2 protein is 904 amino acids in length and contains elements characteristic of a membrane glycoprotein. After cleavage of the predicted 22 amino acid signal sequence, the mature, non-glycosylated protein would have a molecular weight of 98,221. The amino terminal 22 residues contain a core of hydrophobic residues ($Leu_6$ to $Ala_{20}$) preceded by a charged basic reside (Arg at position 2) and an alanine-rich signal peptidase recognition sequence, $Ala_{20}Ser_{21}$-$Ala_{22}$, conforming to rules identified for preferred signal peptidase cleavage sites and the general characteristics of eukaryotic signal peptides (Watson, Nucl. Acid Res. (1984) 12:5145–5164). Protein sequence analysis of the N-terminus of recombinant HSV-1 glycoprotein B identified the first amino acid of the mature Type 1 protein as Ala followed by $Pro_{31}Ser_{32}Ser_{33}Pro_{34}$. Due to the conservation of the 6 amino acids centered around the signal cleavage recognition sequence, we assign $Ala_{23}$ of gB2 as the first amino acid of the mature glycoprotein.

The external hydrophilic region of the protein from $Ala_{23}$ to $Asp_{723}$ contains 8 possible sites for N-linked glycosylation identified by the sequence Asn-X-Thr/Ser where X=any of the 20 amino acids with the possible exception of aspartic acid. By analysis of the predicted secondary structure of gB1, Pellett et al. found 6 of 9 possible glycosylation sites for gB1 on the surface of the protein at junctions of helical or β-sheet structures and therefore likely to be efficient substrates for glycosylation. The remarkable amino acid homology between the Type 1 and 2 proteins suggests that the utilization of potential glycosylation sites is similar.

A comparison of the primary sequences of HSV-1 and HSV-2 glycoprotein B is shown in FIG. 4. Amino acid differences between the Type 2 and Type 1 proteins are highlighted by boxes. Overall the two proteins share a nucleotide and an amino acid homology of 86%. However, the differences appear to be significant, since only 12.5% of the amino acid substitutions between gB1 and gB2 are conservative changes. These differences in primary sequence are clustered in certain regions of the protein resulting in long domains which are identical as well as small regions of marked divergence.

The region of greatest divergence between gB1 and gB2 is the signal sequence. For gB2, the predicted signal sequence is only 22 amino acids in length, as compared to 30 for gB1 strain Patton, and shares only 55% amino acid homology with the Type 1 protein. It is of interest to note that while the length of the entire coding sequence for gB1 and gB2 is the same (904 amino acids) the mature gB2 would be 7 amino acids longer than gB1 due to its shorter signal peptide.

3.2. Expression of qB2 in mammalian cells

Expression of HSV-2 glycoprotein gB has been achieved in COS cells (transient expression) and in CHO cells (stable cell line secreting gB2) transformed with pHS210 alone or cotransformed with pHS210 and a second plasmid containing dhfr.

Figure 10:
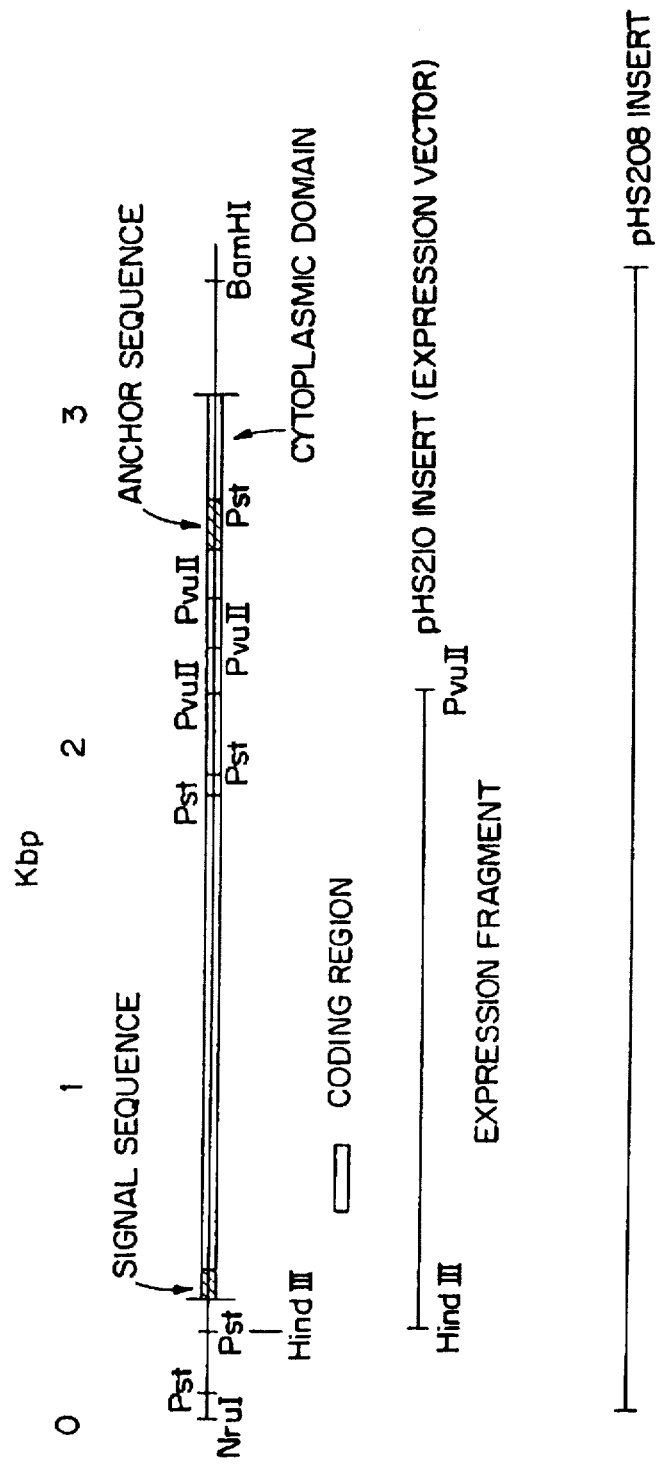
FIG. 10 is a restriction map of gB2, showing the origination of the oligonucleotides inserted into the expression vector.

Plasmid pHS210 was constructed as follows: The entire gene was subcloned as a 3.8 kb NruI-BamHI fragment in pBR322 to generate pHS208. See FIG. 10. The PstI site at the 5' end of the gene, 100 bp to the right (downstream) of the NruI site, was changed to a HindIII site by in vitro mutagenesis in M13. A HindIII to Pvu fragment of 1.9 kb was then inserted into pSV1, which was obtained by digestion of pSV1/dhfr with HindIII and BgIII. See FIGS. 5 and 10. For this cloning step, pHS208 was cut with PvuII and the end repaired to blunt. The molecule was then cut with HindIII and the 1.9 kb HindIII-(PvuII) fragment isolated by gel electrophoresis. Likewise pSV1/dhfr was cut with BgIII, repaired to blunt, cut with HindIII and the 4.85 kb HindIII-BgIII) vector fragment isolated by gel electrophoresis. These two fragments (1.9 kb and 4.85 kb) were ligated together to generate pHS210—the expression plasmid (FIG. 10).

Plasmid pHS210 was used directly to transform COS cells. Expression was detected by immunofluorescence using a gB specific monoclonal antibody, F3 A/B, and also using a commercially available polyclonal anti HSV-2 antibody (DAKO) as the primary antibody screen. Secretion of gB2 into the medium was detected by a gB2-specific ELISA. For this purpose, plates were coated with the monoclonal antibody. Samples of cell culture medium were added to coated plates, then bound gB2 was detected with the rabbit anti HSV-2 polyclonal antibody (DAKO) followed by horseradish conjugated goat anti-rabbit IgG.

For CHO cell transformation plasmid pHS210 was used along with a second plasmid containing dhfr as a selective marker in a cotransfection protocol. Following transfection and propagation in selective media, approximately 100 dhfr⁺ clones were isolated and screened for synthesis and secretion of gB2 using an ELISA assay in which ELISA plates were coated with F3 P/B specific monoclonal antibody. Clone pHS210 #3-1, which had the highest levels of gB secretion, was chosen for further characterization of the gB2 polypeptide. The gB2 protein was detected by labeling with [$^{35}$S]-methionine followed by immunoprecipitation. After a 1 hr pulse, diffuse doublet bands corresponding to polypeptides of 79 Kd and 84 Kd were detected intracellularly. These proteins are larger than the 68,891 dallon size predicted for the 637 residue truncated gene product, and they presumably correspond to partially glycosylated precursors. After a 5 hr chase, no gB2 was detected intracellularly, and an 89 Kd polypeptide was detected in the medium. The size of the mature, fully glycosylated gB2 secreted into the media of clone pHS210 #3-1 is somewhat smaller than the 100 Kd gB1 secreted by pHS114-6 due to the removal from pHS210 of the coding sequence for 94 amino acids included in the gB1 plasmid.

It is evident from the above results that oligonucleotide sequences are provided which can be used in a variety of ways. The oligonucleotide sequences may be used as probes for detecting HSV glycoprotein B or analogous proteins from other members of the herpes virus family. Furthermore, the sequences can be used for the expression of a wide variety of polypeptides, including glycoprotein B precursor, mature glycoprotein B, and functional fragments or domains thereof, which can be joined to sequences other than the naturally occurring sequences to provide hybrid polypeptides and proteins having a wide variety of utilities. The glycoprotein produced by hybrid DNA technology can be used in a wide variety of ways, as a reagent in immunoassays, as a vaccine, as a competitor with HSV for receptor sites, and the like.

4. Vaccine Trials

The utility of vaccines containing gB in protecting against herpes virus infections is illustrated below. In these studies the gB protein was produced by cloning a truncated gB gene from HSV-1 strain Patton into the plasmid pHS114 which was then used to transfect Chinese hamster ovary (CHO) cells. The truncation deletes the 194-carboxyl terminal amino acids including the hydrophobic transmembrane domain and the cytoplasmic region such that the resulting protein is secreted into the culture medium rather being inserted into the cell membrane. The gB protein was purified by sequential steps of lentil lectin chromatography, immunoaffinity chromatography, and concentration by ultrafiltration resulting in a preparation which was 70% homogeneous as determined by SDS polyacrylamide gel electrophoresis.

4.1 Humoral immunity in mice

Outbred female Swiss Webster mice (Simonsen) were immunized on day 1 with a 1:1 mixture of recombinant vaccine preparation and complete Freund's adjuvant. One half of the dose was administered subcutaneously, the other half intraperitoneally. The mice received 5 ug recombinant gB protein synthesized in mammalian cells. Mice were boosted on day 20 with the same dose and vaccine preparations, but incomplete Freund's adjuvant was used to make the emulsion. They were bled by cardiac puncture on day 28. Total lectin affinity purified Patton strain HSV glycoproteins served as a positive vaccine control, and a recombinant Feline leukemia envelope B protein was used as a negative control. A second boost was given on day 41 and animals were bled again on day 53. Sera from the mouse bleeds were collected and assayed for antibody levels by ELISA and plaque reduction neutralization assay. The results of this experiment are summarized in Table 1 below.

TABLE 1

| Experiment 1: Humoral Immunity in Mice | | | | |
|---|---|---|---|---|
| Animal | Immunogen | Dose | ELISA Titer[a] | Neutralization Titer[b] |
| BLEED #1 | | | | |
| 4 | recombinant gB | 5 µg | 1:41750 | n.d[c] |
| 5 | recombinant gB | 5 µg | 1:24547 | 1:640 |
| 6 | env B | 20 µg | <1:10 | <1:20 |

TABLE 1-continued

Experiment 1: Humoral Immunity in Mice

| Animal | Immunogen | Dose | ELISA Titer[a] | Neutralization Titer[b] |
|---|---|---|---|---|
| 7 | total herpes glycoproteins | 20 μg | 1:175 | 1:125 |
| | | BLEED #2 | | |
| 4 | recombinant gB | 5 μg | 1:17507 | n.d.[c] |
| 5 | recombinant gB | 5 μg | 1:24155 | n.d.[c] |
| 6 | env B | 20 μg | <1:10 | n.d.[c] |
| 7 | total HSV glycoproteins | 20 μg | 1:1466 | n.d.[c] |

[a]ELISA with 20 μg/ml total HSV-1 (Patton) glycoproteins as antigen, 50% endpoint.
[b]Plaque reduction neutralization assay with complement. HSV-1 (McIntyre). 50% endpoint.
[c]Not done.

4.2 Protection of mice against virus challenge

The in vivo response of mice to the vaccine candidates was also examined by challenging immunized animals with a lethal dose of virus. Female Swiss Webster mice were immunized with the vaccine candidates. The first injections were done using 5 ug recombinant gB mixed in an equal volume of complete Freund's adjuvant. One half the dose was given intraperitoneally, the other half subcutaneously on day 1. Mice were boosted 2 and 4 weeks later in the same manner with incomplete Freund's adjuvant in the emulsion. Control animals received 20 ug of lectin purified total HSV glycoproteins previously described or 23 ug of a control yeast plus CHO cell extract. Mice were bled one week after the final boost by cardiac puncture. Sera were collected and assayed for antibody titers by ELISA. Animals were challenged 15 days later with $3.25 \times 10^8$ pfu of HSV-1 (Patton) (2 $LD_{50}$'s) given intraperitoneally. They were monitored for a 14 day time period for the appearance of clinical signs or morbidity. Mice surviving the virus challenge were observed for 10 additional days at which time they were bled and the sera examined by ELISA. The results of this experiment are summarized in Table 2 below.

TABLE 2

Experiment 2: Protection of mice against virus challenge

| Group | Animal | Immunogen | Dose | ELISA Titer[a] | % Survival[b] | ELISA Titer[c] |
|---|---|---|---|---|---|---|
| 2 | A | recombinant gB | 5 μg | 1:1928 | 80 (4/5) | |
| | B | | | 1:1097 | | 1:2660 |
| | C | | | 1:2660 | | 1:1539 |
| | D | | | 1:1614 | | 1:9641 |
| | E | | | 1:13737 | | 1:7573 |
| 3 | A | total HSV glycoproteins | 20 μg | 1:2339 | 100 (4/4) | 1:1928 |
| | B | | | 1:172 | | 1:965 |
| | C | | | 1:2660 | | 1:5488 |
| | D | | | 1:2883 | | 1:3026 |
| 4 | A | control cell extracts | 23 μg | <1:25 | 20 (1/5) | 1:734 |
| | B | | | 1:85 | | |
| | C | | | 1:51 | | |
| | D | | | <1:25 | | |
| | E | | | <1:25 | | |

[a]ELISA with 10 μg/ml total HSV-1 (Patton) glycoproteins as antigen, 50% endpoint.
[b]Percent of mice surviving 14 days after challenge. (Number of surviving mice over total number.)
[c]Sera tested from mice surviving virus challenge.

4.3 Protection of guinea pigs against initial and recurrent genital herpes

Vaccines containing a mixture of HSV glycoproteins were prepared from HSV-1 strain Patton or HSV-2 strain 333 infected Vero cells by lentil lectin Sepharose chromatography using the method of Respess et al. *J. Virol. Methods* (1984) 8:27. These mixtures contained for HSV-1, approximately 36% gB1 and 26% gD1, and for HSV-2, approximately 22% gB2 and 4.5% gD2, as percent of total protein. In addition the mixtures contained as well as high concentrations of gC, lower amounts of gE and gG plus a mixture of unidentified HSV and Vero cell proteins.

Eighty, 350 to 400 gram female Hartley guinea pigs (Charles River Breeding Laboratory, Wilmington, Mass.) were immunized in the hind footpads 60 and again 30 days prior to intravaginal inoculation with 5.7 $\log_{10}$pFu HSV-2, MS strain (Stanberry et al., *Intervirology* (1985) 24:226). Animals were immunized as follows: Group I—unimmunized control; Group II—control yeast and CHO cell protein extracts (32 μg) plus complete Freund's adjuvant (CFA); Group V—HSV-1 gB (20 μg) plus CFA; Group VI—HSV-1 glycoprotein mixture (50 μg) without adjuvant; Group VII—HSV-1 glycoprotein mixture (50 μg) plus CFA; Group VIII—HSV-2 glycoprotein mixture (50 μg) without adjuvant; Group IX—HSV-2 glycoprotein mixture (50 μg) plus CFA. All vaccines were adjusted to a total volume of 0.1 ml and administered with an equal volume of adjuvant or 0.9% saline.

The course of initial genital HSV-2 infection was evaluated by genital skin lesion scores, incidence of urinary retention and titer of virus in vaginal swab samples (Stanberry et al., *J. Infect. Dis.* (1982) 146:397). The following skin lesion score was used: 0=no disease; 1=redness or swelling; 2=a few small vesicles; 3=several large vesicles; 4=several large ulcers with maceration. The clinical course of initial infection is summarized in Table 3 and FIG. 11. Compared to the unimmunized and cell extract control groups the frequency of both skin disease and urinary retention was reduced in all vaccinated groups of animals. The recombinant glycoprotein preparations reduced the severity of genital skin disease by 93% for gB while the glycoprotein mixtures administered with adjuvant completely eliminated any manifestations of skin disease. It was further observed that viral replication in the genital tract was also altered by prior immunization with a glycoprotein preparation (Table 3). The peak virus titer in vaginal secretions was significantly reduced in all treatment groups. The animals immunized with gB had peak HSV-2 titers less than 1% of the titers observed in unimmunized animals, while those guinea pigs receiving the mixture of HSV-1 or HSV-2 glycoproteins plus CFA had peak titers less than 0.01% of control values. Likewise, the magnitude of viral replication throughout initial infection as represented by the area under the log virus titer-day curve was also significantly lower for these groups (p>0.01). It has been previously reported that prior HSV infection also reduced the magnitude of viral replication in the genital tract resulting from intravaginal HSV-2 rechallenge (Stanberry et al. *J. Infect. Dis.* (1986) 153:1055). However, prior immunization with the HSV-1 or the HSV-2 glycoprotein mixture plus adjuvant resulted in a greater reduction in the magnitude of viral replication after HSV-2 inoculation (Table 3) than was observed in animals intravaginally rechallenged with HSV-2 after recovery from initial genital HSV-2 infection (mean area under the log virus titer day curve presented in FIG. 1 of Stanberry, ibid. initial infection=36.5±1.5; rechallenge=17.0±2.4 (p>0.01)). These data suggest that immunization with a subunit vaccine may potentprotecprovide greater protection from HSV infection than that elicited by previous infection. This report, as well as the study by Berman et al., *Science* (1984) 227:1490 indicates that prior immunization with HSV glycoprotein vaccines provides substantial protection against the clinical manifestations of intravaginal HSV-2 in guinea pigs. As shown here, recombinant HSV-1 gB affords similar protection to that provided by the HSV-1 or HSV-2 glycoprotein mixture.

immunized animals did not exhibit recurrent herpetic disease while 57% and 94% of guinea pigs immunized with the HSV-1 or HSV-2 glycoprotein mixture with adjuvant were protected from developing recurrent herpetic infections. Furthermore, the animals that did exhibit recurrent disease after immunization with either gB or the HSV-1 glycoprotein mixture plus adjuvant had significantly fewer recurrences and recurrent episodes of significantly shorter duration than did control animals (p>0.05). These observations indicate that administration of a subunit HSV glycoprotein vaccine may have a very substantial impact on the natural history of recurrent herpetic disease.

TABLE 3

Clinical and virologic course of initial genital Herpes Simplex virus type 2 infection in guinea pigs

| Group | Vaccine[a] | Concentr. μg | Incidence of Skin Lesions | Skin Lesion Severity[b] | Incidence of Urinary Retention | Incidence of Viral Replication[c] | Magnitude of Viral Replication[d] |
|---|---|---|---|---|---|---|---|
| I | Unimmunized | — | 16/16 | 18.9 | 16/16 | 16/16 | 29.0 |
| II | Cell extract control | 32 | 10/10 | 25.7 | 10/10 | 10/10 | 30.3 |
| V | HSV-1 gB | 20 | 1/8 | 1.2 | 1/8 | 8/8 | 13.8 |
| VI | HSV-1 total glycoproteins | 50 | 5/7 | 3.0 | 4/7 | 7/7 | 19.9 |
| VII | HSV-1 total glycoproteins | 50 | 0/7 | 0 | 0/7 | 7/7 | 4.1 |
| VIII | HSV-2 total glycoproteins | 50 | 6/10 | 3.5 | 3/10 | 10/10 | 16.9 |
| IX | HSV-2 total glycoproteins | 50 | 0/8 | 0 | 0/8 | 8/8 | 3.3 |

[a]Groups II, VII, IX administered with Complete Freund's Adjuvant: Groups I, VI, VIII administered without adjuvant.
[b]Calculated as the area under the mean lesions score day curve.
[c]Defined by recovery of virus from vaginal swab samples on at least two occasions 24 hours apart.
[d]Calculated as the area under the mean virus titer day curve.

The data indicates, however, that the greatest protection against vaginal HSV-2 replication was provided by immunization with the glycoprotein mixtures and that the effects were greatly enhanced by the presence of adjuvant.

The effect of immunization prior to initial infection on the subsequent pattern of recurrent genital HSV-2 infection between days 15 to 62 post intravaginal challenge is summarized in Table 4. We have previously reported that all animals surviving initial infection exhibit spontaneous recurrent herpetic lesions on the external genital skin (Stanberry et al. (1985) supra). This study demonstrates that immunization with HSV glycoprotein vaccine prior to HSV-2 challenge can protect animals from developing recurrent genital HSV-2 infection. For example, 33% of gB The antibody response to HSV-1 and HSV-2 antigens after immunization and intravaginal HSV-2 challenge is shown in Table 5.

TABLE 4

Effect of viral glycoprotein immunization on the pattern of recurrent genital Herpes Simplex virus type 3 infection in guinea pigs[a]

| Vaccine | Adjuvant[b] | Animals with Recurrent Lesions | Lesion Days per Animal[c,d] | Episodes per Animal[c,e] | Lesion Days/Episode per Animal[f] |
|---|---|---|---|---|---|
| Unimmunized | No | 4/4 | 16.3 ± 1.9 | 7.8 ± 0.9 | 2.1 ± 0.2 |
| HSV-1 gB (20 μg) | Yes | 4/6 | 1.7 ± 0.8 | 1.3 ± 0.8 | 1.5 ± 0.3 |
| HSV-1 glycoproteins (50 μg) | No | 7/7 | 9.9 ± 2.4 | 5.6 ± 0.9 | 1.6 ± 0.2 |
| HSV-1 glycoproteins (50 μg) | Yes | 3/7 | 0.7 ± 0.4 | 0.6 ± 0.3 | 1.3 ± 0.3 |
| HSV-2 glycoproteins (50 μg) | No | 8/8 | 8.9 ± 3.2 | 3.4 ± 1.0 | 1.9 ± 0.4 |
| HSV-2 glycoproteins (50 μg) | Yes | 1/8 | 0.5 ± 0.5 | 0.5 ± 0.5 | 1.0 ± 0 |

[a]Animals were immunized in the hind footpad 60 and again 30 days prior to intravaginal HSV-2 inoculation. After recovery from initial infection, animals were examined daily from day 15 through day 62 post inoculation for evidence of recurrent herpetic lesions.
[b]Complete Freund's adjuvant.
[c]Mean ± standard error, calculated using all animals.
[d]Days when a recurrent lesion was observed.
[e]An episode of recurrent disease was defined as lesion day(s) preceded and followed by a day without any lesion.
[f]Mean ± standard error, calculated using only animals with recurrent lesions.

Sera were collected from animals 30 days after the second immunization, but prior to infection (day 0), and again 30 days after intravaginal HSV-2 inoculation (day 30) and were assayed for anti-HSV antibodies by both ELISA and virus neutralization plaque reduction assays. The ELISA method was a modification of the method of Morahan et al. *Infect. Immun.* (1981) 32:180 utilizing either the lectin purified HSV-1 or HSV-2 glycoprotein mixture as the coating antigen and assigning a 50% endpoint as the ELISA titer. The plaque reduction assay was similar to that described by Bernstein et al. *Virology*, infra except that all sera were tested in the presence of exogenously added complement. All animals seroconverted (Table 5) following infection but the magnitude of the antibody response by day 30 was significantly greater in animals immunized with gB or the HSV-1 or HSV-2 glycoprotein mixture plus adjuvant than in the unimmunized controls (p>0.001). It was apparent that animals with preexisting HSV antibodies (seropositive on day 0) had milder initial disease and less frequent recurrent infections than seronegative animals. When one controlled for the variable introduced by treatment group, analysis of the data revealed the total number of days animals experienced recurrent herpetic lesions was negatively related to the antibody titer prior to intravaginal HSV-2 challenge (day 0) (p=0.04 by analysis of covariance). However, similar analysis failed to demonstrate any correlation between antibody response on either day 0 of day 30 and any measure of the severity of initial infection (i.e. peak lesion score, area under the lesion score-day curve, incidence or duration of urinary retention).

Guinea pigs immunized with HSV glycoproteins were protected against the clinical manifestations of initial HSV-2 genital infection and experienced a reduced incidence, frequency and duration of recurrent herpetic disease. The extent of protection was influenced by the nature of the glycoprotein vaccine, the immunizing dose and the coadministration of adjuvant.

In the second experiment designed to test the effect of a variation in route of immunization and adjuvant (complete Freund's adjuvant versus alum) 81 female Hartley guinea pigs were immunized as noted in the following table.

| Group | Treatment | Dose | Adjuvant | Route | N |
|---|---|---|---|---|---|
| 2 | CHO cell extract | 8 µg | Alum | SQ* | 12 |
| 3 | HSV-2 total pP2 | 50 µg | Freund's | Footpad | 9 |
| 4 | gP2 | 50 µg | Alum | Footpad | 9 |
| 5 | gP2 | 50 µg | Alum | SQ | 8 |
| 6 | HSV-1 gB | 40 µg | Alum | SQ | 8 |
| 1 | Untreated | — | — | — | 18 |

*Subcutaneously

Group 2 was immunized twice on days −63 and −28. All other groups were immunized thrice on days −58, −42 and −21. On day 1 all pigs were intravaginally inoculated with $5 \times 10^5$ pfu HSV-2 strain MS. Group 6 was immunized with mammalian produced glycoproteins. The course of the initial genital HSV-2 infection was evaluated as before with the results shown in Table 6. The experiment shows that the choice of both route and adjuvant modifies the outcome of the primary disease; alum is a less effective adjuvant than

TABLE 5

| | | | Anti-Herpes Simplex virus antibody[a] | | | | | |
|---|---|---|---|---|---|---|---|---|
| | | | $Log_{10}$ Neutralizing Titer | | $Log_{10}$ ELISA Titer[b] | | $Log_{10}$ ELISA Titer[c] | |
| Groups | Vaccine | Number | Day 0 | Day 30 | Day 0 | Day 30 | Day 0 | Day 30 |
| I | Unimmunized | 10 | 0 | 2.6 ± 1.8 | 0 | 3.3 ± 2.5 | 0 | 3.3 ± 2.3 |
| II | Control cell Extract (32 µg) | 7 | 0 | 2.5 ± 1.9 | 0 | 3.6 ± 3.3 | ND[d] | ND |
| V | HSV-1 gB (20 µg) | 7 | 3.9 ± 3.3 | 3.8 ± 3.2 | 6.3 ± 5.8 | 6.2 ± 5.4 | 4.9 ± 4.6 | 4.7 ± 4.0 |
| VI | HSV-1 glycoproteins (50 µg) | 7 | 3.3 ± 2.3 | 3.3 ± 2.6 | 4.5 ± 4.0 | 4.5 ± 3.8 | ND | ND |
| VII | HSV-1 glycoproteins (50 µg) | 7 | 4.4 ± 3.6 | 4.1 ± 3.4 | 7.0 ± 6.4 | 6.7 ± 6.2 | 5.1 ± 4.9 | 4.8 ± 4.3 |
| VIII | HSV-2 glycoproteins (50 µg) | 10 | 2.9 ± 2.2 | 3.1 ± 2.4 | 4.3 ± 3.8 | 4.2 ± 3.5 | 3.6 ± 3.1 | 3.8 ± 3.2 |
| IX | HSV-2 glycoproteins (50 µg) | 7 | 4.4 ± 3.9 | 4.1 ± 3.5 | 6.7 ± 6.4 | 6.4 ± 6.0 | 6.1 ± 4.9 | 4.8 ± 4.3 |

[a]Values are mean ± standard error on sera collected prior to and 30 days after intravaginal HSV-2 inoculation.
[b]To HSV 1 antigens.
[c]To HSV 2 antigens.
[d]ND = Not done.

Interestingly, the antibody titers on day 30 (but not day 0) were negatively correlated with the peak virus titer in vaginal secretions (p=0.003) and the area under the virus titer-day curve (FIG. 1B) (p=0.007 by analysis of covariance).

complete Freund's adjuvant for these antigens and the subcutaneous route is less effective than the footpad. The pattern of recurrent disease for these same animals is shown in Table 7 and the conclusion are essentially the same as noted for primary disease.

TABLE 6

Effect of HSV glycoprotein vaccines on primary HSV 2 genital infection in guinea pigs

| Group | Treatment[d] | Dose μg | Adjuvant[b] | Route[c] | Animals with Skin Lesions | Severity of Skin Disease[d] | Duration of Urinary Retention[e] | Mortality[f] |
|---|---|---|---|---|---|---|---|---|
| 1 | None | | | | 19/19 | 14.8 ± 1.0 | 5.4 ± 0.4 | 32 |
| 2 | CHO Extract | n | Alum | SQ | 11/11 | 11.9 ± 1.4 | 5.3 ± 0.3 | 27 |
| 3 | gP2 | 50 | CFA | FP | 0/6 | 0 | 0 | 0 |
| 4 | gP2 | 50 | Alum | FP | 4/7 | 0.7 ± 0.5 | 0.6 ± 0.6 | 0 |
| 5 | gP2 | 50 | Alum | SQ | 5/8 | 2.3 ± 0.9 | 3.0 ± 1.0 | 22 |
| 6 | gB | 40 | Alum | SQ | 7/8 | 2.8 ± 1.1 | 3.9 ± 0.7 | 0 |

[a]Vaccines administered 9,6 and 3 was prior to intravaginal HSV-2 inoculation with 5.3 $\log_{10}$ pfs HSV-2 (MS Strain) except group 3 which was immunized 9 and 4 weeks prior to viral challenge.
[b]Alum = Aluminum phosphate (10%); CFA = complete Freund's adjuvant.
[c]SQ = Subcutaneously in hindlimb; FP hindlimb footpad.
[d]Mean area under the skin lesion score-day curve ± error.
[e]Mean days ± standard error.
[f]Deaths within 14 days of HSV-2 inoculation.

TABLE 7

Effect of HSV glycoprotein vaccination on the pattern of recurrent genital HSV-2 infection in guinea pigs[a]

| Group | Treatment | N | Days Lesions Observed[b] (Mean ± SE) | Recurrent Episodes[c] (Mean ± SE) | Days/ Episodes |
|---|---|---|---|---|---|
| 1 & 2 | Control | 9 | 20.6 ± 2.4 | 10.9 ± 1.2 | 1.9 |
| 3 | qP2/CFA/ FootPad | 6 | 3.2 ± 1.3 | 2.3 ± 1.0 | 1.4 |
| 4 | qP2/Alum/ Footpad | 0 | 3.0 ± 0.8 | 2.4 ± 0.6 | 1.3 |
| 5 | gP2/Alum/ SQ | 5 | 11.8 ± 2.0 | 7.0 ± 0.9 | 1.7 |
| 6 | gB/Alum/ | 6 | 13.8 ± 2.4 | 7.5 ± 1.4 | 1.8 |

[a]Animals examined for recurrent lesions day 14–92 after intravaginal HSV-2 challenge.
[b]All groups except gP2/Alum/SQ significant: different from control (p < 0.05).
[c]All groups except gD significantly different from control p < 0.05).

Although the foregoing invention has been described in some detail by way of illustration and example for purposes of clarity and understanding, it will be obvious that certain changes and modifications may be practiced within the scope of the appended claims.

The following E. coli HB101 strains were deposited at the A.T.C.C., where the plasmid indicate the plasmid employed to transform the strain pHS112; pHS114 (gB1 mammalian); pHS127A (gB1 yeast); pHS203; and pHS206 (gB2) on April 4, 1984, and assigned Accession Nos. 39649–39653, respectively, where the nature of the plasmid is indicated in parentheses and the number refers back to the number employed in the Experimental section.

What is claimed is:

1. A method of producing a recombinant polypeptide comprising:

(a) providing a DNA construct for the expression of a glycosylated polypeptide in a eucaryotic host cell, said construct comprising:

(i) an oligonucleotide sequence substantially free of natural flanking regions, encoding a glycoprotein B (gB) of Herpes Simplex virus (HSV) or a functional fragment thereof; and (ii) transcriptional and translational regulatory sequences flanking said oligonucleotide sequence, wherein said regulatory sequences at the 5'-end regulate initiation and said regulatory sequences at the 3'-end regulate termination, and wherein at least one of said regulatory sequences is other than a HSV regulatory sequence;

(b) transforming a eucaryotic host cell with the DNA construct of step (a); and (c) culturing said transformed host cell of step (b) under conditions whereby said gB or said functional fragment thereof is expressed.

2. The method of claim 1 wherein the HSV is HSV-1.

3. The method of claim 1 wherein the HSV is HSV-2.

4. The method of claim 1 wherein said host cell is a yeast cell.

5. The method of claim 1 wherein said host cell is a mammalian cell.

6. A method of producing a diagnostic reagent for the detection of Herpes Simplex Virus infection, said method comprising:

(a) providing a DNA construct for the expression of a glycosylated polypeptide in a eukaryotic host cell, said DNA construct comprising:

(i) an oligonucleotide sequence substantially free of natural flanking regions, encoding a glycoprotein B (gB) of Herpes Simplex virus (HSV) or functional fragments thereof; and (ii) transcriptional and translational regulatory sequences flanking said oligonucleotide sequence, wherein said regulatory sequences at the 5'-end regulate initiation and said regulatory sequences at the 3'-end regulate termination, and wherein at least one of said regulatory sequences is other than a HSV regulatory sequence;

(b) transforming a eucaryotic host cell with the DNA construct of step (a); and (c) culturing said transformed host cell of step (b) under conditions whereby said gB or said functional fragment thereof is expressed;

(d) recovering said expressed gB or said functional fragment thereof; and (e) combining said recovered gB or said functional fragment thereof with a detectable label.

7. The method of claim 6 wherein the HSV is HSV-1.

8. The method of claim 6 wherein the HSV is HSV-2.

9. The method of claim 6 wherein said host cell is a yeast cell.

10. The method of claim 6 wherein said host cell is a mammalian cell.

* * * * *